(12) United States Patent
Vandenberghe

(10) Patent No.: US 9,036,899 B2
(45) Date of Patent: May 19, 2015

(54) METHOD FOR QUANTIFYING LOCAL BONE CHANGES

(75) Inventor: Bart Vandenberghe, Brussels (BE)

(73) Assignee: KATHOLIEKE UNIVERSITEIT LEUVEN, Leuven (BE)

(*) Notice: Subject to any disclaimer, the term of this patent is extended or adjusted under 35 U.S.C. 154(b) by 237 days.

(21) Appl. No.: 13/703,493

(22) PCT Filed: Jun. 14, 2011

(86) PCT No.: PCT/EP2011/059860
§ 371 (c)(1),
(2), (4) Date: Dec. 11, 2012

(87) PCT Pub. No.: WO2011/154559
PCT Pub. Date: Dec. 15, 2011

(65) Prior Publication Data
US 2013/0094740 A1  Apr. 18, 2013

(30) Foreign Application Priority Data
Jun. 11, 2010  (GB) .................................. 1009725.1

(51) Int. Cl.
*G06K 9/00* (2006.01)
*G06T 11/00* (2006.01)
(Continued)

(52) U.S. Cl.
CPC .............. *G06T 11/003* (2013.01); *A61B 5/055* (2013.01); *A61B 6/14* (2013.01); *A61B 6/4085* (2013.01);
(Continued)

(58) Field of Classification Search
USPC ........................................ 348/42–60; 382/154
See application file for complete search history.

(56) References Cited

U.S. PATENT DOCUMENTS 6,429,884 B1 * 8/2002 Budz et al. ..................... 715/848
7,596,257 B2 * 9/2009 Kim .............................. 382/131
(Continued)

FOREIGN PATENT DOCUMENTS

| GB | 2 453 177 A | 4/2009 |
|---|---|---|
| WO | 0222014 A1 | 3/2002 |
| WO | 2008/000278 A1 | 1/2008 |

OTHER PUBLICATIONS

Scherf et al., "A New High-Resolution Computed Tomography (CT) Segmentation Method for Trabecular Bone Architectural Analysis," American Journal of Physical Anthropology, 2009, pp. 39-51, vol. 140, Wiley-Liss, Inc.

(Continued)

*Primary Examiner* — Alex Liew
(74) *Attorney, Agent, or Firm* — Bacon & Thomas, PLLC

(57) ABSTRACT

A method and system for volumetric quantification of local bone changes includes the steps of loading at least a first and second (cone-beam) computed tomography three dimensional image, registering the first three dimensional image and second three dimensional image to one coordinate system, selecting a region of interest in one of the first three dimensional image or the second three dimensional image. For the first three dimensional image and the second three dimensional image, segmenting the local bone within the region of interest by segmenting voxels related to air and/or soft tissues within the region of interest and attributing these voxels to an outside region, while the volume formed by the remaining volume represent the local bone or the local bone with soft tissue, and calculating of the volume of local bone in the first three dimensional image and the volume of local bone in the second three dimensional image and subtracting the first volume from the second volume and defining the difference as the local bone change or the change in local bone with soft tissue.

15 Claims, 9 Drawing Sheets

(51) Int. Cl.
*A61B 6/14* (2006.01)
*A61B 6/00* (2006.01)
*G06T 7/00* (2006.01)
*A61B 5/055* (2006.01)

(52) U.S. Cl.
CPC ............... *A61B 6/466* (2013.01); *A61B 6/469* (2013.01); *A61B 6/486* (2013.01); *A61B 6/5217* (2013.01); *A61B 6/5235* (2013.01); *G06T 7/0016* (2013.01); *G06T 2207/10081* (2013.01); *G06T 2207/20101* (2013.01); *G06T 2207/20141* (2013.01); *G06T 2207/30036* (2013.01)

(56) References Cited

U.S. PATENT DOCUMENTS

| | | | |
|---|---|---|---|
| 7,987,079 B2* | 7/2011 | Billinghurst et al. | 703/7 |
| 8,244,028 B2* | 8/2012 | Kuo et al. | 382/154 |
| 8,253,778 B2* | 8/2012 | Atsushi | 348/42 |
| 2005/0010106 A1 | 1/2005 | Lang et al. | |
| 2005/0018886 A1* | 1/2005 | Kim | 382/128 |
| 2006/0262969 A1 | 11/2006 | Matsumoto | |
| 2009/0034790 A1* | 2/2009 | Song et al. | 382/103 |
| 2011/0169861 A1* | 7/2011 | Suzuki et al. | 345/632 |

OTHER PUBLICATIONS

Rizzo et al., "Autotmatic Segmentation of Cortical and Trabecular Components of Bone Speciments Acquired by pQCT," 30th Annual International IEEE EMBS Conference, Aug. 20-24, 2008, pp. 486-489.

Buie et al., "Automatic Segmentation of cortical and trabecular compartments based on a dual threshold technique for in vivo micro-CT bone analysis," BONE, 2007, pp. 505-515, vol. 41, Elsevier.

International Search Report PCT/EP2011/059860 issued Sep. 23, 2011.

International Preliminary Report on Patentability in PCT/EP2011/059860, dated Oct. 16, 2012.

* cited by examiner

METHOD FOR QUANTIFYING LOCAL BONE CHANGES

FIELD OF THE INVENTION

The present invention relates to methods and systems for volumetric quantification of local bone or soft tissue loss or gain and methods for determining a region of interest in 3D image data. Bone/soft tissue loss is an important clinical criterion for determination of the success-rate of the following dental therapies: periodontal therapy, bone augmentation or grafting techniques, implant therapy, endodontic therapy or orthodontic therapy.

BACKGROUND OF THE INVENTION

Periodontal disease is the most common oral disorder in the elderly population and showing an increasing incidence with age. It consists of several disorders of the periodontium (tissues surrounding the teeth), including gingivitis and periodontitis, which are chronic infectious diseases. The presence of certain bacteria initiate plaque and calculus formation supra- and subgingival (above and under the gums), which affects the soft tissues (gums) surrounding the teeth and causes inflammation. This gingivitis (inflamed gums) associated with bleeding of the gums, can progress to periodontitis when soft tissue attachment loss and/or supporting bone loss is seen. This bone loss (resulting in pocket formation between the teeth and the remaining soft tissues or bone) may affect one to all teeth and eventually, when left untreated, lead to tooth loss. Furthermore, bacteria in the plaque may cause caries reaching the pulpal tissues of the teeth and cause periapical (around the apex or root point of the tooth) inflammation with periapical bone loss.

Many studies have shown the importance of early detection of periodontal disease, in relation to the prevention of tooth loss and/or the patient's general health. The amount of bone loss detected will determine the treatment choice, ranging from a more conservative approach to drastic extraction of a "lost" tooth. Diagnostic tools are therefore crucial for accurate assessment of the periodontal status. Currently, intra-oral projection radiographs are used to radiographically assess periodontal bone loss. However, these radiographs project all periodontal structures on top of each other, which make differentiation of buccal and oral bone hardly impossible.

In addition, if the x-ray's are not pointed perpendicular to the receptor, bone levels can be misinterpreted because of projection errors.

Thus, one of the main drawbacks of intra-oral radiography is overlap of anatomical structures and lack of three-dimensional (3D) information. This often hinders a true distinction between the buccal and lingual cortical plate and complicates the evaluation of periodontal bone defects, especially the infrabony lesions, also denoted as craters, and furcation involvements (bone loss at the furcation). Depending on the pattern of these infrabony defects, different treatment methods are at hand. For instance, when a local crater has enough supporting bony walls, a membrane can be attached onto its surrounding walls, while bone or bone alternatives are condensed into the cavity of the crater, with as goal the remodelling of this new bone with disappearing or shrinking of the crater (=bone gain). Another example is rootplaning (deep cleaning of roots of the teeth with instruments) to stop further bone loss. To determine the result of these therapies, the current 2D projection radiographs form an additional problem. Using digital radiographs, a radiograph before and 6 months after therapy can be taken and subtracted from one another to see small radiographic density changes. Unfortunately, it is critical to use the same projection angle at both moments, so individualized bite blocks need to be fabricated per patient to follow up the bone. Also, this digital subtraction radiography (DSR) does not provide any 3D information.

The same principle applies when investigating bone lesions around the root end (apex) of a tooth, where 2D projection radiographs often causes misdiagnosis since the buccal and oral bony plates may project onto these local lesions inside the bone. Therefore, recent studies have examined the use of 3D imaging modalities for periodontal diagnosis, as described by Vandenberghe et al. in "Detection of periodontal bone loss using digital intra-oral and CT images: an in-vitro assessment of bony and/or infrabony defects" in Dentomaxillofac Radiol. 2008 (37) 252-260. Besides traditional medical CT images, novel 3D cone beam computed tomography (CBCT) images which are low dose CT images, have recently been introduced in the dental field. It has been shown that CBCT helps in diagnosis of crater and furcation problems and therefore may help in the treatment follow-up of these periodontal defects. When periodontal disease progresses, severe bone loss can lead to tooth loss. Oral implants as replacement-therapy for one or more teeth has become a very predictable surgical procedure and is therefore now routinely used in the modern dental practice. One of the classic criteria for measuring the success-rate of implant-therapy is a local bone loss smaller then 0.2 mm per year, after the first year (Albrektsson et al. in Dent. Clin. North Am. 1986 (30) 151-174). This bone loss therefore needs a precise radiographic follow-up using an individualized set-up, existing of aiming devices and bite-blocks, just like periodontal defects around teeth. Although the critical importance of reducing projection errors with two-dimensional radiographs and using an optimal radiographic protocol, the current literature describing radiographic follow-up in details is sparse. Inter- and intra-observer variability is seldom explored and new three-dimensional techniques are still not commonly used. On 2D projection radiographs, it is namely only possible to measure the vertical bone height (for bone loss assessment), while the bone volume and its remodelling constitutes a three-dimensional process. This indicates that the previously mentioned criteria should be updated.

The same problem is seen when using bone augmentation techniques (bone grafting and ridge preservation). Implant-therapy has several obstacles that can influence its use or success-rate. Beside medico-social factors and the associated bone quality of the patient, the therapy choice is strongly dependent of the remaining bone quantity or the available bone volume at the implant-site. If insufficient bone volume remains, the surgeon can nowadays choose out of many techniques, to prepare the site for implant therapy. These so called bone augmentation techniques can be subdivided into many categories, for instance based upon the recipient site (sinus floor or alveolar ridge) or based upon its complexity (from alveolar ridge preservation techniques after tooth extraction to interpositional bone grafts). In addition, the bone material itself can be autogenous, allogenic, xenogenic (usually bovine) bone or replaced by alloplastic materials for bone growth, with or without combination with membranes for guided bone regeneration and/or BMPs (bone promoting proteins) and PRPs (platelet rich plasma). The success-rate of all these techniques has often been described in the literature, following-up the clinical and radiographic parameters like complications, augmentation failure and implant failure, etc . . . but contradictory results are often demonstrated. This indicates that the choice of augmentation and implant therapy is very complex, and that in addition it is complicated by the continuous technological innovation—on implant as well as bone augmentation level. Also here, the criterion bone loss needs to be put in the context of three dimensions, where bone loss and its remodelling happen in 3D. Again, the current methodology to determine success-rate for these techniques should be questioned. For instance, while Meijndert et al in Clin. Oral Implants Res. 2008 (19) 1295 utilise 2D projection radiographs to determine bone loss and success, Pieri et al in J. Periodontol. 2008 (79) 2093 use 2D measurements on sectional CT slices, both techniques having many limitations.

The recent introduction of low dose three-dimensional imaging has drastically changed the face of dentistry. Low dose cone beam computed tomography (CBCT) has many advantages compared to its big brother, the conventional multi-slice CT scanner, which opened the door to many more clinical applications, as described in Vandenberghe et al. in Eur. Radio. 2010 (20) 2637. Unfortunately, volumetric quantification of bone still has only been employed a few times and rarely for volumetric follow-up of bone loss. Agbaje et al. describe in "Bone healing after dental extractions in irradiated patients: a pilot study on a novel technique for volume assessment of healing tooth sockets" published online in Clin. Oral. Investig. (2008), the use of volumetric quantification for volumetric follow-up of bone loss. The morphology or 3D topography of periodontal defects can be determined using 3D imaging, but also here periodontal disease is a dynamic 3D process that manifests as infrabony craterlike bone loss of periodontal bone surrounding a tooth, which needs follow-up in time. The same situation is seen here, where crater therapy using membranes or bone materials should be followed-up and validated in 3D in stead of on 2D images. Often widths and heights are measured on 2D slices, as e.g. discussed in Chen et al. J. Periodontal 2008 (79) 401, which is better than on projection radiographs, but still this shows a severe limitation since all the above bone remodelling processes are in three dimensions. Agbaje et al. (2008) demonstrated that CBCT is an ideal imaging modality for volumetric determination of the healing of extraction sockets. But one needs also to explore the exact volume determination method or segmentation method more thoroughly. Most dentomaxillofacial segmentation studies are based on manually drawing or coloring the desired structures on each slice in the 3D space. This is very cumbersome. Determination of the border of a structure can be done in many different ways and is dependent of several factors, as e.g. described in Suri et al. Handbook of biomedical image analysis, Volume II: Segmentation models, Springer (2005) 111-182. For instance, manual slice by slice segmentation of structures can be very user dependent and time consuming, especially when two volumes in time need to be processed. Also the 3D scanning of the volume of interest (for instance the head) is usually much larger than the actual region of interest (ROI) (for instance one tooth). Especially the segmentation of bone grafts can be quite difficult because of limited visibility on (CB)CT volumes, as indicated for example in Beaman et al. In Radiographics 2006 (26) 373.

For bone augmentation techniques, implant follow-up or periodontal bone loss follow-up, current literature only uses clinical measurements (width and/or height) on 2D projection radiographs or 2D slices of a 3D volume. Only a few attempts were taken towards volumetric determination using conventional CT, as described in Beaman et al. In Radiographics (2006) 26 p373 and Feichtinger et al. In Cleft. Palate Craniofac. J. (2007) 44 p142, but non using low dose CBCT. Feichtinger et al (2007) follow-up bone volumes but they use a commercial segmentation package (and manually segment out or delineate manually slice-by-slice the bone) without further deepening of the methodology or variables used. Current literature therefore lacks in two main aspects: follow-up of bone volumes and clinical relevance of the segmentation method used. Without an accurate, efficient and universal volume determination method, the optimal bone grafting technique for implant therapy can not be investigated. It thus becomes difficult using the existing methods for answering for example the question which bone graft method of a given selection results in less bone loss. The same goes for implant therapy: which implant results in less bone loss? Or even for periodontal therapy: which technique of crater therapy is more beneficial? Therefore, there is a need for a method for quantification of bone loss (or changes) and implementation on all these clinical indications solving one or more of the above problems.

Current diagnostic approaches have been broadened from 2D projection radiographs to 3D (CB)CT volumes (which are stacks of 2D slices), especially in implant dentistry. However, this bone remodelling is a dynamics process over time, which needs an accurate follow-up. Until now, current follow-up of the changes of alveolar bone is done on 2D radiographs or 2D slices.

A first class of solutions relates to bone follow-up on 2D radiographs. FIG. 1 is a schematic representation of two radiographs at time 1 and 2. Currently, the two ways of measuring bone loss around a tooth or dental implant on 2D projection radiographs is through bone level measurements on radiograph 1 and 2 (double arrows in FIG. 4) or through digital subtraction radiography (DSR) when digital sensors are used and DSR software is at hand.

In addition to the fact that this is only a part of the bone loss that can be assessed (height loss at 1 point while the volume should be assessed), projection errors may project the bone at differently than the actual situation. Also, radiographs at time 1 and 2 need to have almost equal projection geometry to be able to subtract or even compare both radiographs. Individual bite blocks (waxed imprints of the region of interest's teeth) can be fabricated and mounted onto aiming devices for the intra-oral radiographs.

A second class of solutions relates to bone follow-up based on 2D slices of a 3D volume. FIG. 2 is a schematic representation of two computed tomography (CT) scans at time 1 and 2. Notice that the second scan can have a different coordinate system than the first scan.

When measuring bone loss on 2D slices of a 3D volume, a good standardization is still necessary where certain anatomical markers need to be indicated in order to compare measurements on scan 1 and 2. For instance, one can measure the bone loss from the cemento-enamel junction (junction of the crown of the tooth and the root) at the extreme left and right side of the tooth until the alveolar crest. Measurements can now be done on adjacent slices to see if there is a difference in bone loss through the whole bone volume surrounding the tooth. In addition, horizontal measurements can now also be made, where the width (arrows in FIG. 2) of the alveolar ridge can be measured, which is not possible on a 2D projection. The major problem here is that a lot of measurements per tooth need to happen, with again the precise standardization required. This makes assessment of the whole volume almost impossible. Therefore, in current research, measurements are chosen at certain levels (width and height). Again, this results in insufficient volume information for follow-up and it is rather time consuming.

Because of all these limitations it is also very difficult to validate periodontal therapies—from rootplaning to bone augmentation and implant therapy. Which methods results in the least bone loss? This makes it of course also very difficult to precisely follow-up periodontal patients.

Ideally, the whole volume is measured to follow-up bone loss. This volume determination or segmentation can be done slice by slice by selecting the desired region (region of interest, ROI) on both scans (see FIG. 3).

In this scenario, an experienced observer can use the computer mouse to manually trace the region of interest in each slice. Drawbacks are of course the intensive labour required, operator bias and difficulty in obtaining reproducible results. In this way, volume 1 and 2 will both be influenced by these limitations, resulting in inadequate follow-up of bone volumes.

SUMMARY OF THE INVENTION

It is an object of the present invention to provide a method for volumetric quantification of local bone or soft tissue loss which makes it possible to solve one or more of the problems of the state of the art. It is an advantage of embodiments according to the present invention that efficient methods using semi-automatic segmentation and/or image registration are provided. The image registration may comprise transforming datasets, for instance a bone graft site scan just after surgery and after 6 months, to 1 coordinate system.

It is an advantage of at least some embodiments that algorithms can be applied for determining and comparing precisely the region of interest where the bone loss may be present. It is an advantage of at least some embodiments of the present invention that accurate and fast methods and systems for selecting and comparing bone volume regions of interest are provided.

It is an advantage of at least some embodiments of the present invention that a small or minimized region of interest can be selected because of the number of artifacts that typically is present in e.g. (CB)CT and because of intensity deviations in pre and post scans. It is an advantage that for example not the whole jaw or no large part of the jaw is to be taken into account as this could contain too many errors for accurate segmentation.

It is an advantage of at least some embodiments of the present invention that a universal method for selecting region of interest is provided thus bringing a standardized method for accurate follow-up of bone change and for validating the outcome of several clinical therapies in Periodontology. The latter may be especially advantageous for local bone change around a tooth or implant or for bone augmentation techniques in a small region.

The above objective is accomplished by a method and device according to the present invention.

In one aspect the present invention relates to a method for volumetric quantification of local bone changes comprising the steps of loading at least a first and second computed tomography three dimensional image, registering said at least a first three dimensional image and second three dimensional image to one coordinate system, selecting a region of interest in one of said first three dimensional image or said second three dimensional image, for said first three dimensional image and said second three dimensional image, segmenting the local bone within the region of interest by segmenting voxels related to air and/or soft tissues within the region of interest and attributing these voxels to an outside region, while the volume formed by the remaining volume represent the local bone or the local bone with soft tissue, and calculating of the volume of local bone in the first three dimensional image and the volume of local bone in said second three dimensional image and subtracting said first volume from said second volume and defining the difference as the local bone change or the change in local bone with soft tissue.

Selecting a region of interest in one of the first three dimensional image or the second three dimensional image may comprise the steps of selecting a set of anatomical landmarks in said one of the first three dimensional image or the second three dimensional image, determining a set of clipping planes which construct a volume forming the region of interest in the three dimensional image on the basis of said anatomical landmarks, and removing all data from the three dimensional image outside the region of interest.

Determining a set of clipping planes may comprise determining a set of 6 clipping planes.

Selecting anatomical landmarks may comprise selecting at least one or a combination of a first landmark being a most caudal or cranial root apex of the teeth neighbouring the local bone volume to be determined, a second landmark being the most cranial or caudal tooth cervix of a teeth neighbouring the local bone volume to be determined, whereby, if an alveolar crest is missing partly in the region of interest, a most caudal or cranial tooth cervix can be chosen, a third and fourth landmarks being most proximal edges of a teeth's roots neighbouring the local bone volume to be determined, whereby in case of a neighbouring implant, a most proximal edge of the implant body or its abutment can be chosen in such a way that no metal of the implant is present in the final region of interest and whereby in case a direct neighbour is missing, a next element in the arch can be used for the landmarks selection, a fifth landmark being a most buccal bony edge of the region of interest and a sixth landmark being a most oral bony edge of the region of interest.

Selecting the anatomical landmarks may comprise selecting at least all of a first landmark being a most caudal or cranial root apex of the teeth neighbouring the local bone volume to be determined, a second landmark being the most cranial or caudal tooth cervix of a teeth neighbouring the local bone volume to be determined, whereby, if an alveolar crest is missing partly in the region of interest, a most caudal or cranial tooth cervix can be chosen, a third and fourth landmarks being most proximal edges of a teeth's roots neighbouring the local bone volume to be determined, whereby in case of a neighbouring implant, a most proximal edge of the implant body or its abutment can be chosen in such a way that no metal of the implant is present in the final region of interest and whereby in case a direct neighbour is missing, a next element in the arch can be used for the landmarks selection a fifth landmark being a most buccal bony edge of the region of interest or a sixth landmark being a most oral bony edge of the region of interest.

The landmarks for the upper jaw may comprise the spina nasalis or inferior border of the nasal cavity or maxillary sinus, and/or the landmarks for the lower jaw may comprise the inferior mandibular cortical border, inferior or superior border of the inferior alveolar canal, incisive canal or mental foramen or genial tubercles.

Selecting a set of anatomical landmarks may comprise taking into account whether bone change is followed for a case where no teeth are present.

Selecting a set of anatomical landmarks may comprise taking into account whether bone change is followed around radiolucent lesions of the jaws, including periapical lesions.

Selecting a set of anatomical landmarks may comprise taking into account whether bone change is followed such that soft tissues surrounding the local bone is included in the region of interest.

Determining clipping planes may comprise determining at least one or a combination of a first clipping plane being constructed by defining a plane through the first landmark point said plane parallel with the axial direction, second clipping plane being constructed by defining a plane through the second landmark point said plane parallel with the axial direction, a third and fourth clipping plane being constructed by defining a plane through the third landmark point parallel with the sagittal direction and a plane through the fourth landmark points parallel with the sagittal direction, a fifth clipping plane being constructed by defining a plane through the fifth landmark point said plane parallel with the coronal direction, and a sixth clipping plane being constructed by defining a plane through the sixth landmark point said plane parallel with the coronal direction.

Selecting the set of landmarks comprises selecting said six landmarks and wherein determining clipping planes may comprise determining all of a first clipping plane being constructed by defining a plane through the first landmark point said plane parallel with the axial direction, a second clipping plane being constructed by defining a plane through the second landmark point said plane parallel with the axial direction, a third and fourth clipping plane being constructed by defining a plane through the third landmark point parallel with the sagittal direction and a plane through the fourth landmark points parallel with the sagittal direction, a fifth clipping plane being constructed by defining a plane through the fifth landmark point said plane parallel with the coronal direction, or a sixth clipping plane being constructed by defining a plane through the sixth landmark point said plane parallel with the coronal direction.

The present invention also relates to a system for volumetric quantification of local bone changes, the system comprising an input means for receiving at least a first and second computed tomography three dimensional image, a processing means configured for registering the at least first and second computed tomography three dimensional image, for selecting a region of interest in one of the first or the second computed tomography three dimensional image, for segmenting the local bone within the region of interest in the first computed tomography three dimensional image and the second computed tomography three dimensional image, by segmenting voxels related to air and/or soft tissues within the region of interest and attributing the voxels to an outside region, while defining the remaining volume as representing the local bone or the local bone with soft tissue, and for calculating the volume of the local bone or the local bone with soft tissue in the first and the second tomographic three dimensional image and substracting the first volume from the second volume thereby defining the difference as the local bone change or the change in local bone with soft tissue. The system also comprises an output means for outputting the local bone change or the change in local bone with soft tissue.

The system may be adapted for performing a method as described above.

The present invention also relates to a method for selecting a region of interest in a computed tomography three dimensional image comprising selecting a set of anatomical landmarks in the computed tomography three dimensional image, determining a set of clipping planes which construct a volume forming the region of interest in the three dimensional image on the basis of said anatomical landmarks, and removing all data from the three dimensional image outside the region of interest.

Selecting the anatomical landmarks may comprise selecting at least one or a combination of a first landmark being a most caudal or cranial root apex of the teeth neighbouring the local bone volume to be determined, a second landmark being the most cranial or caudal tooth cervix of a teeth neighbouring the local bone volume to be determined, whereby, if an alveolar crest is missing partly in the region of interest, a most caudal or cranial tooth cervix can be chosen, a third and fourth landmarks being most proximal edges of a teeth's roots neighbouring the local bone volume to be determined, whereby in case of a neighbouring implant, a most proximal edge of the implant body or its abutment can be chosen in such a way that no metal of the implant is present in the final region of interest and whereby in case a direct neighbour is missing, a next element in the arch can be used for the landmarks selection, a fifth landmark being a most buccal bony edge of the region of interest or a sixth landmark being a most oral bony edge of the region of interest. Determining clipping planes comprises determining at least one or more of a first clipping plane being constructed by defining a plane through the first landmark point said plane parallel with the axial direction, second clipping plane being constructed by defining a plane through the second landmark point said plane parallel with the axial direction, a third and fourth clipping plane being constructed by defining a plane through the third landmark point parallel with the sagittal direction and a plane through the fourth landmark points parallel with the sagittal direction, a fifth clipping plane being constructed by defining a plane through the fifth landmark point said plane parallel with the coronal direction, and a sixth clipping plane being constructed by defining a plane through the sixth landmark point said plane parallel with the coronal direction.

The present invention also relates to a computer program product for, when executing on a processing means, carrying out one of the methods as described above.

The present invention also relates to a data carrier for storing a computer program product, and/or to the transmission of such a computer program product over a local or wide area network.

The present invention furthermore relates to an image or volumetric image obtained using a method for quantifying bone loss as described above or a method for selecting a region of interest as described above.

According to one aspect, a method or system for volumetric quantification of local bone changes as described above is provided wherein the first and second image is an optical three dimensional image, wherein attributing voxels is attributing a subset of pixels of the optical three dimensional image, and whereby the remaining volume represents the local bone with soft tissue.

The present invention also relates to a method for volumetric quantification of local bone/soft tissue loss comprising loading a first and second computed tomography 3D image, registering said first 3D image and said second 3D image to one coordinate system, selecting a region of interest in one of said first 3D image or said second 3D image, segmenting, for said first 3D image and said second 3D image, the local bone within the region of interest by segmenting the grey zones related to air and/or soft tissues within the region of interest, these grey zones are then attributed to the outside region, while the remaining volume represents the local bone and calculating the volume of local bone in said first 3D image and the volume of local bone in said second 3D image and subtracting said first volume from said second volume and defining the difference as the local bone change. The volume representing the local bone may be the volume representing the local bone with or without soft tissues. The computed tomography 3D images may be cone-beam computed tomography 3D images or optical 3D images.

In a preferred embodiment the selecting of a region of interest in a 3D image comprises the following steps: selecting a set of anatomical landmarks in said 3D image; on the basis of said anatomical landmarks constructing 6 clipping planes (clipping box) which construct a volume in said 3D image, said volume being the region of interest; and removing all data from the 3D image outside the region of interest. Removing all data from the 3D image outside the region of interest may be a cropping process.

In another preferred embodiment the anatomical landmarks which form the basis of the clipping planes comprise a first landmark as the most caudal (for the upper jaw) or cranial (for the lower jaw) root apex of the teeth neighbouring the local bone volume to be determined. A second landmark may be the most cranial (for the upper jaw) or caudal (for the lower jaw) tooth cervix (cemento-enamel junction) of the teeth neighbouring the local bone volume to be determined. If the alveolar crest is missing partly in the region of interest, the most caudal (for the upper jaw) or cranial (for the lower jaw) tooth cervix (cemento-enamel junction) can be chosen. Third and fourth landmarks may be the most proximal edges of the teeth's roots neighbouring the local bone volume to be determined. In case of a neighbouring implant, the most proximal edge of the implant body or its abutment can be chosen in such a way that no metal of the said implant is present in the final region of interest. In case a direct neighbour is missing, the next element in the arch can be used for the landmarks selection. A fifth landmark may be the most buccal bony edge of the region of interest (lying between landmarks 1 and 2). A sixth landmark may be the most oral (palatal for upper jaw and lingual for lower jaw) bony edge of the region of interest (lying between landmarks 1 and 2). In this preferred embodiment the clipping planes may be constructed as follows: A first clipping plane is constructed by defining a plane through the first landmark point said plane parallel with the axial direction. A second clipping plane is constructed by defining a plane through the second landmark point said plane parallel with the axial direction. A third and fourth clipping plane are constructed by defining a plane through the third landmark point parallel with the sagittal direction and a plane through the fourth landmark points parallel with the sagittal direction. A fifth clipping plane is constructed by defining a plane through the fifth landmark point said plane parallel with the coronal direction. A sixth clipping plane is constructed by defining a plane through the sixth landmark point said plane parallel with the coronal direction.

In yet another preferred embodiment said anatomical landmarks specified above may vary depending on suspecting bone loss or gain more cranial (for the upper jaw) or more caudal (for the lower jaw) than the root apices. The suggested landmarks for the upper jaw are then the spina nasalis or inferior border of the nasal cavity or maxillary sinus. The suggested landmarks for the lower jaw are then the inferior mandibular cortical border, inferior or superior border of the inferior alveolar canal, incisive canal or mental foramen or genial tubercles. It may also vary depending on whether bone loss or gain is followed when no teeth are present. The suggested landmarks for the upper jaw are then the spina nasalis or inferior border of the nasal cavity or maxillary sinus and the most caudal point of the alveolar crest surrounding the desired area. The suggested landmarks for the lower jaw are then the inferior mandibular cortical border, inferior or superior border of the inferior alveolar canal, incisive canal or mental foramen or genial tubercles and the most cranial point of the alveolar crest surrounding the desired area.

It may also vary depending on whether bone loss or gain is followed around radiolucent lesions of the jaws, including periapical lesions. The landmarks are then the most cranial, caudal, mesial, distal, vestibular and oral border points of the lesion. If associated to present teeth, the axis of the tooth may be used to determine these extremities.

It may also depend on whether it is desired to include the soft tissues surrounding the local bone. Landmark five becomes then the most buccal soft tissue edge of the region of interest (lying between landmarks 1 and 2). Landmark six becomes then the most oral (palatal for upper jaw and lingual for lower jaw) soft tissue edge of the region of interest (lying between landmarks 1 and 2). If the desired soft tissues partially lie outside the second clipping plane, landmark two may become the most caudal (for the upper jaw) or most cranial (for the lower jaw) soft tissue point.

It is a further object of the present invention to provide a method for selecting a region of interest in a (cone beam) CT scan or 3D image which makes it possible to solve one or more of the problems of the state of the art. The method of the present invention for selecting a region of interest in a (cone beam) CT scan or 3D image comprising the following steps selecting a set of anatomical landmarks in said 3D image, on the basis of said anatomical landmarks constructing 6 clipping planes (clipping box) which construct a volume in said 3D image, said volume being the region of interest and removing all data from the 3D image outside the region of interest (cropping)

In a preferred embodiment the anatomical landmarks of the method of the present invention comprise a first landmark as the most caudal (for the upper jaw) or cranial (for the lower jaw) root apex of the teeth neighbouring the local bone volume to be determined. A second landmark may be the most cranial (for the upper jaw) or caudal (for the lower jaw) tooth cervix (cemento-enamel junction) of the teeth neighbouring the local bone volume to be determined. If the alveolar crest is missing partly in the region of interest, the most caudal (for the upper jaw) or cranial (for the lower jaw) tooth cervix (cemento-enamel junction) can be chosen. The third and fourth landmarks may be the most proximal edges of the teeth's roots neighbouring the local bone volume to be determined. In case of a neighbouring implant, the most proximal edge of the implant body or its abutment can be chosen in such a way that no metal of the said implant is present in the final region of interest. In case a direct neighbour is missing, the next element in the arch can be used for the landmarks selection. The fifth landmark may be the most buccal bony edge of the region of interest (lying between landmarks 1 and 2). A sixth landmark may be the most oral (palatal for upper jaw and lingual for lower jaw) bony edge of the region of interest (lying between landmarks 1 and 2).

The clipping planes may be constructed as follows: A first clipping plane is constructed by defining a plane through the first landmark point said plane parallel with the axial direction. A second clipping plane is constructed by defining a plane through the second landmark point said plane parallel with the axial direction. A third and fourth clipping plane are constructed by defining a plane through the third landmark point parallel with the sagittal direction and a plane through the fourth landmark points parallel with the sagittal direction. A fifth clipping plane is constructed by defining a plane through the fifth landmark point said plane parallel with the coronal direction. A sixth clipping plane is constructed by defining a plane through the sixth landmark point said plane parallel with the coronal direction.

In yet another preferred embodiment said anatomical landmarks specified above may vary depending on suspecting bone loss or gain more cranial (for the upper jaw) or more caudal (for the lower jaw) than the root apices. The suggested landmarks for the upper jaw are then the spina nasalis or inferior border of the nasal cavity or maxillary sinus. The suggested landmarks for the lower jaw are then the inferior mandibular cortical border, inferior or superior border of the inferior alveolar canal, incisive canal or mental foramen or genial tubercles. It may depend on whether bone loss or gain is followed when no teeth are present. The suggested landmarks for the upper jaw are then the spina nasalis or inferior border of the nasal cavity or maxillary sinus and the most caudal point of the alveolar crest surrounding the desired area. The suggested landmarks for the lower jaw are then the inferior mandibular cortical border, inferior or superior border of the inferior alveolar canal, incisive canal or mental foramen or genial tubercles and the most cranial point of the alveolar crest surrounding the desired area. It may depend on whether bone loss or gain is followed around radiolucent lesions of the jaws, including periapical lesions. The landmarks are then the most cranial, caudal, mesial, distal, vestibular and oral border points of the lesion. If associated to present teeth, the axis of the tooth may be used to determine these extremities. It may depend on whether it is desired to include the soft tissues surrounding the local bone. Landmark five becomes then the most buccal soft tissue edge of the region of interest (lying between landmarks 1 and 2). Landmark six becomes then the most oral (palatal for upper jaw and lingual for lower jaw) soft tissue edge of the region of interest (lying between landmarks 1 and 2). If the desired soft tissues partially lie outside the second clipping plane, landmark two may become the most caudal (for the upper jaw) or most cranial (for the lower jaw) soft tissue point.

Particular and preferred aspects of the invention are set out in the accompanying independent and dependent claims. Features from the dependent claims may be combined with features of the independent claims and with features of other dependent claims as appropriate and not merely as explicitly set out in the claims. These and other aspects of the invention will be apparent from and elucidated with reference to the embodiment(s) described hereinafter.

Figure 1:
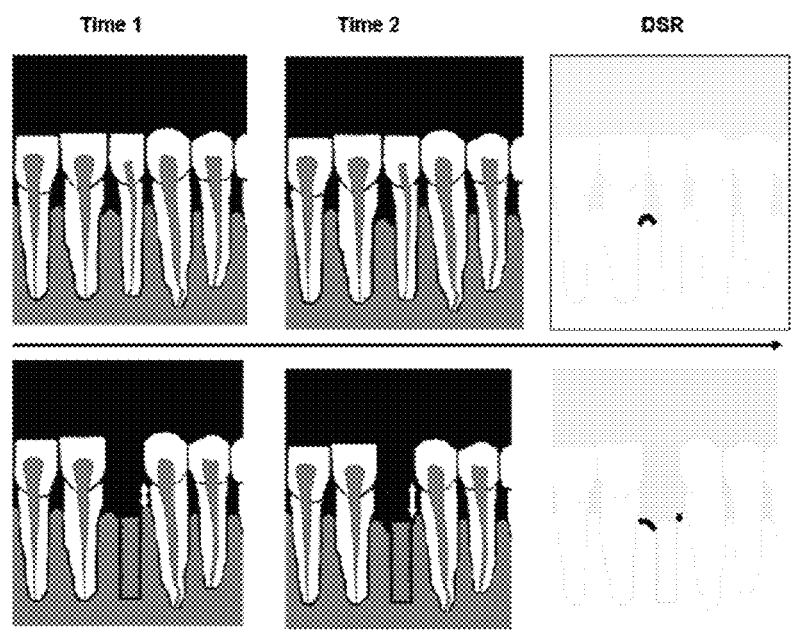
FIG. 1 illustrates a schematic view of digital subtraction radiography for periodontal bone loss around a tooth (up) or an implant (down), as known from prior art.
Figure 2:
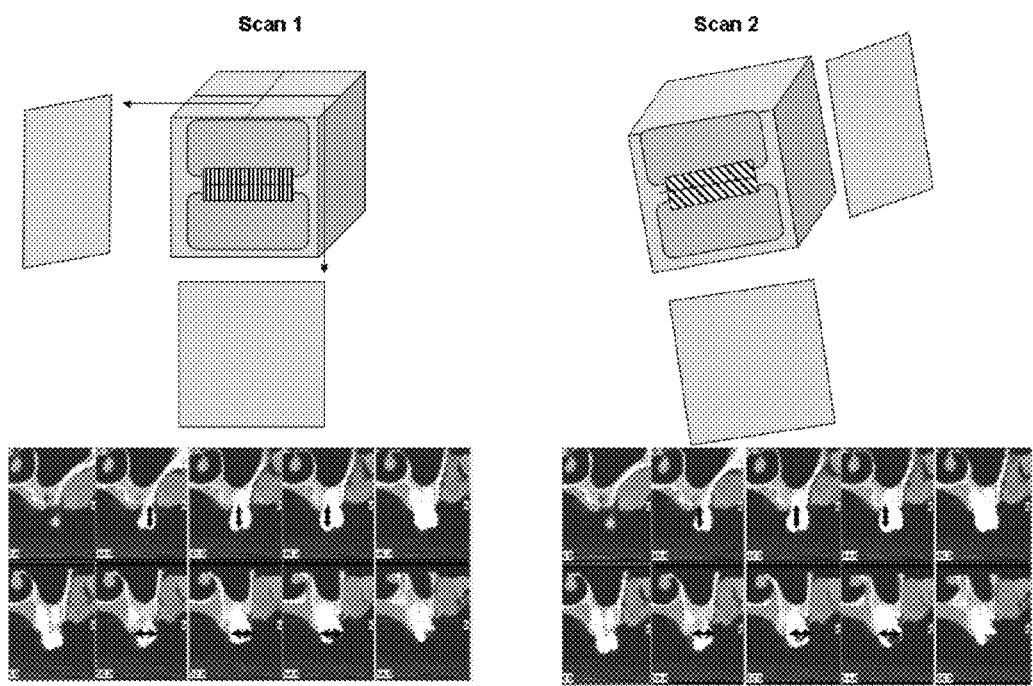
FIG. 2 illustrates a schematic overview of two CT scans at time 1 and 2. Measurements on the 2D slices of scan 1 can be compared to measurements on the slices of scan 2 (horizontal and vertical double arrows), as used in prior art.
Figure 3:
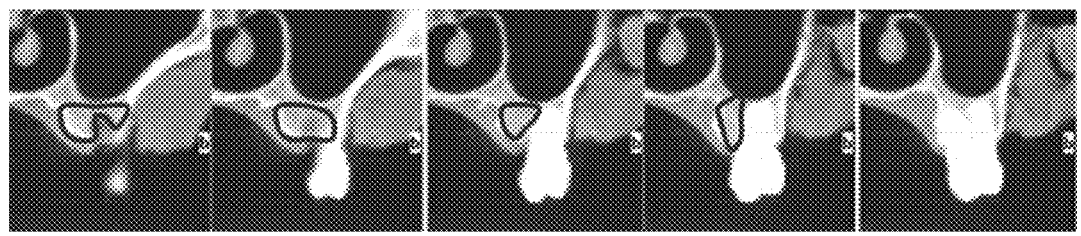
FIG. 3 indicates manual slice-by-slice segmentation of the ROI. On each slice a region is drawn, which is part of the ROI and which will be added to one another to form a volume of interest (VOI), as used in prior art.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments according to the present invention reference is made to a computed tomography three dimensional image, reference is made to a computed tomography image extending in three dimensions, to a computed tomography image built up of a set of voxels or to a corresponding data set comprising the values corresponding with the intensity of the voxels of the corresponding image. Such an image also may be referred to as a scan.

Methods and systems according to embodiments of the present invention advantageously can make use of one or more image processing algorithms.

One image processing algorithm that may be used is region growing, allow the selection of a ROI using seed points. In region growing, seed points are used to locate the structure to be segmented. Then, from these seed points on, the region is expanded to neighbouring pixels or voxels, with a criterion to include the neighbouring regions based on image intensity values. This makes an easy and fast selection of the ROI possible. As it is often not easy to exactly differentiate between the different oral structures (teeth, bone, soft tissues, . . . ), further correction techniques may be used including manual slice by slice correction using small selection tools to come to a more accurate segmented volume. Especially on CBCT volumes, which have less contrast resolution (differentiation between tissues with only small differences in densities), grey values of certain important structures to be segmented from one another can lie very close together. For instance, soft tissues from the lip and from the gums will be attributed the same grey value and can thus not be differentiated.

Figure 4:
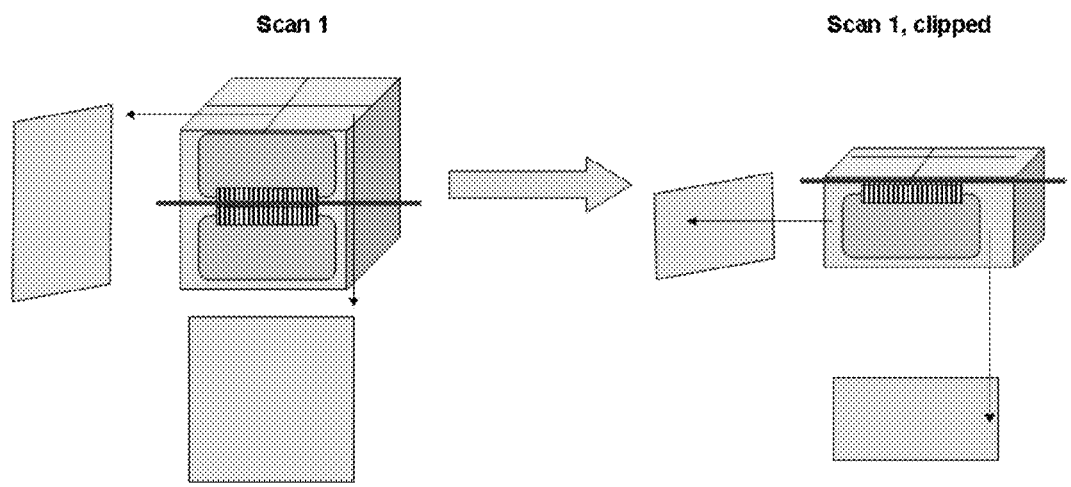
FIG. 4. indicates clipping of unnecessary information or volume (=selecting the region of interest or ROI), as can be used in embodiments according to the present invention.

Another algorithm that may be used is registration. When using these algorithms on a dataset at time 1 and time 2, the segmentation may differ on both scans as the ROI may be segmented differently in scan 2 than 1 because of the above mentioned problems. The two datasets may have different coordinate systems (volumes are a bit tilted compared to each other) because of different patient alignment when taking the scans, which influences the ROI selection but also the different grey values assigned. Therefore, registration algorithms have been developed to align both structures and transfer them to the same coordinate system. This registration is based on mutual information where it is assumed that two structures with the same density are similar and have the same image intensity values. In this way, the post scan (at time 2) can be automatically translated and rotated in order to overlap the pre scan (at time 1). Algorithms for registration based on mutual information as such are known. Another example of an algorithm that can advantageously be used in embodiments of the present invention is clipping or cropping, whereby the volume of interest is reduced. As often, the scanned volume is much larger than the desired ROI, it is easier to first reduce the volume to a desired region. This clipping cuts off unnecessary information (see FIG. 4). Note that this clipping is purely a visualization tool. The undesired information is made invisible. A cropping of the image is also possible but here the undesired data will be deleted.

Clipping is also a typical tool used in commercially available software packages where users can pre-select a region, for instance the lower jaw (in stead of both jaws), by drawing a box on the 3D slices. It allows to only display the structures wanted.

In a first aspect, the present invention relates to a method for volumetric quantification of local bone changes which comprises a series of steps comprising segmentation and registration for following up local bone volumes. It is an advantage of embodiments that a largely or fully automated method is provided, resulting in a good accuracy of the method whereby less user-dependent errors are introduced. The method may make use of a particular clipping based approach. The method may be a computer-implemented method and it may be implemented on a software platform, or in hardware. A graphical user interface may be provided thus rendering a user friendly solution for visualization and analysis. The method typically comprises the step of loading at least two computed tomography three dimensional images e.g. cone-beam computed tomography data for example recorded at different moments in time. The data may correspond with pre- and post-scans, it is scans taken before and after a specific period in time or event. The method also comprises a registration step of the at least two computed tomography three dimensional images. The method further comprises a step of selecting the region of interest, whereby a particular approach for clipping and cropping may be used. In a further step, segmentation of the local bone is performed. Finally also calculation of the amount of bone loss is performed.

The influence of the different variables has been researched in-vitro using simulated bone defects in a dry skull with soft tissue simulation and in cadavers with soft tissues. It is an advantage of embodiments according to the present invention that, by using registration, a more efficient and/or more accurate segmentation can be performed, i.e. a segmentation less prone to errors. The registration using mutual information allows to overlap both scans which makes the ROI clipping/cropping easier, since the selection of the ROI can now only happen on one computed tomography three dimensional image, e.g. the pre-scan (scan 1). The coordinates of the selected ROI can then automatically be transferred to the other computed tomography three dimensional image, e.g. scan 2 or the post-scan. The segmentation method has also been researched and region growing has been found to be more predictable than thresholding (selecting only the grey values corresponding bone) since the latter is prone to errors in grey values (histogram) in the different computed tomography three dimensional images, e.g. pre- and post-scan. Also when using a particular ROI clipping method according to an embodiment of the present invention a set of voxels, sometimes referred to as grey zone, corresponding to air (or soft tissues) can be determined which can easily be used for marking of seed-points. In this way, the bone is indirectly segmented, by segmentation out the grey zone. The method and system according to embodiments of the present invention allows this segmentation automatically on both scan, which reduces the workload. This clipping method is based on anatomical landmarks which has been tested in-vitro. The 3D clipping box (superior and inferior clipping plane, medial and lateral clipping plane, anterior and posterior clipping plane) can be moved towards these anatomical landmarks for ROI selection. The data is then automatically cropped to the ROI (or volume of interest, VOI). Finally, after bone segmentation, both volumes can automatically be calculated and subtracted from one another, resulting in the accurate determination and visualization of the bone changes (loss or gain) area.

By way of illustration, embodiments of the present invention not being limited thereto, an example of a method for quantifying bone loss according to an embodiment of the present invention will further be described, embodiments of the present invention not being limited thereto. The exemplary method indicates standard and optional features and advantages of embodiments of the present invention.

In a first step, the exemplary method comprising loading of at least two different computed tomography three dimensional images. The two different computed tomography three dimensional images may correspond with computed tomography scans. Loading may comprises loading the three dimensional images into a platform. The computed tomography three dimensional images may be computed tomography data recorded at different moments in time, e.g. before and after an event, and may be referred to as PRE and POST scans. These scans can be derived from a cone beam computed tomography unit or a conventional CT. Any CT volumes can namely be used, but especially low dose protocols of CBCT are advantageous as these are already often used in dentistry. Usually these scanned volumes are in the form of a stack of DICOM (Digital Imaging and Communications in Medicine) slices and since MevisLab® has its own 3D format, the pre- and post- scans may first need to be converted. Thus, there are two main actions: the loading of the pre- and post-scan and the conversion to a suitable format for the following steps. The loaded scans can be displayed in two main windows next to one another in the form of an orthogonal 2D slice, which can be scrolled through to visualize the entire volume.

The said CBCT or CT data may as well be obtained using modified scanning protocols, for instance by retracting the soft tissues while performing the 3D scan, or be merged with other data types like optical surface models.

In a second step, the method comprises registration of the different computed tomography three dimensional images, i.e. transferring the data to one coordinate system, e.g. by transferring one of the images to the coordinate system of the other image. Registration of the data sets may comprise transferring the data sets to one coordinate system based on mutual information. In this way, both scans are loaded on top of each other, which makes the ROI selection easier and limited to 1 scan. For this, the MIRIT® software is used, which implements an algorithm for geometric alignment of 3D medical image volumes. It computes fully automated the spatial transformation that maps points in one volume to their corresponding points in another volume. Since we are trying to align two bony structures, which are rigid anatomical structures, the process used is called rigid transformation, with no use of skewing and scaling. The registration used here is more extended and based on maximization of mutual information, where a maximal overlap is looked for in the histograms. A few parameters can be adjusted like the subsampling of the data or number of iterations for the registration depending on the need. In the field "Histogram", the amount of bins can be raised, which computes the histogram with more bins, and thus with more information (but a greater calculation time). The "ExINeg" function excludes negative values since CT images often have negative values assigned to the background. When registering, the floating image moves along the reference image to find the best match. With the parameter "SubSampling" the operator can change with how many pixels the floating image moves along the reference image. The higher this number, the least accurate the registration will be. The third option is the "Parameters" box, which allows the user to change two values for changing the duration or accuracy of the registration: the "number of iterations" and the "multiresolution". The number of iterations can be raised if no acceptable registration has been accomplished. The parameter multiresolution is used to raise the speed of the registration.

The result of the registration process can be seen in 3D (the surface of the registered bony volumes) but also on a 2D overlay orthogonal view (axial, coronal or sagittal can be chosen), where the information of one scan can be marked by a color and overlayed on the other scan. Furthermore, a 2D synchroview is also at hand, which shows the two registered scans in two neighbouring windows. This allows investigating the accuracy of the registration using a pointer which indicates the corresponding points in the two scans.

Variations of the MIRIT algorithm may also be used for registration of the two pre and post datasets. Nevertheless it should only be based on rotation and translation to avoid shear. In this way, manual registration may also be used.

In a third step, the method comprises selecting of the region of interest. The latter may for example be performed using a clipping method as described in more detail below. Using the clipping (and cropping) method, the user will be able to limit the volume to be segmented to the area of interest. This is an important steps, since it would be very inaccurate to start segmentation on the whole volumes given the nature of (CB) CT scans (artifacts, varying grey levels etc.).

Figure 5:
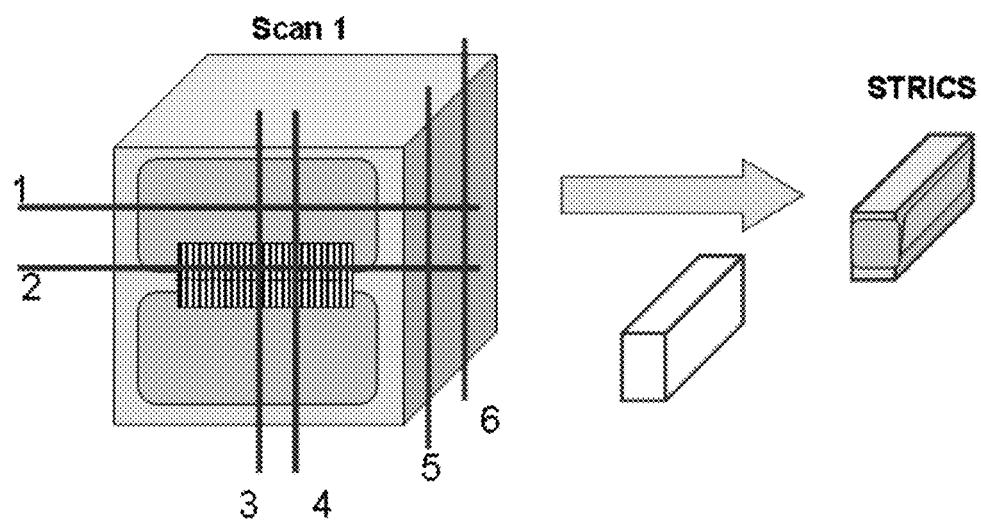
FIG. 5 indicates region of interest (ROI) selection according to embodiments of the present invention. Six clipping axes form a 3D region of interest selection box. 1) superior (cranial) clipping plane 2) inferior (caudal) clipping plane 3) medial clipping plane 4) lateral clipping plane 5) anterior clipping plane 6) posterior clipping plane.
Figure 6:
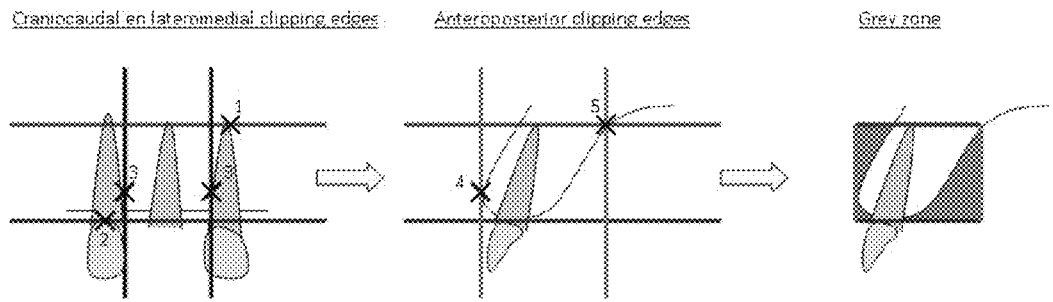
FIG. 6 illustrates a method for clipping a region of interest for the upper jaw (incisors) as can be used in embodiments according to the present invention. 1=most caudal neighbouring tooth-apex, 2=most cranial neighbouring tooth-cervix, 3=least medial and lateral contour of the neighbouring roots, 4=most buccal bone-edge, 5=most palatal bone-edge, grey zone=air and soft tissues covering the bone.
Figure 12:
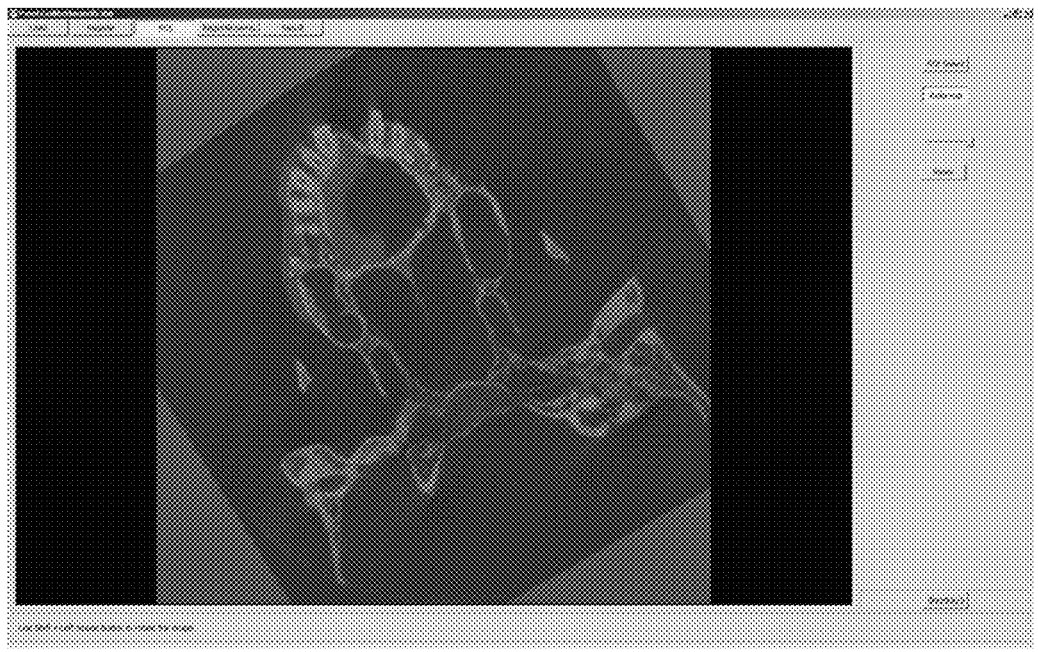
FIG. 12 illustrates rotation (reformatting) of the registered scans for assisting in obtaining correct ROI selection, as can be used in embodiments of the present invention.
Figure 13:
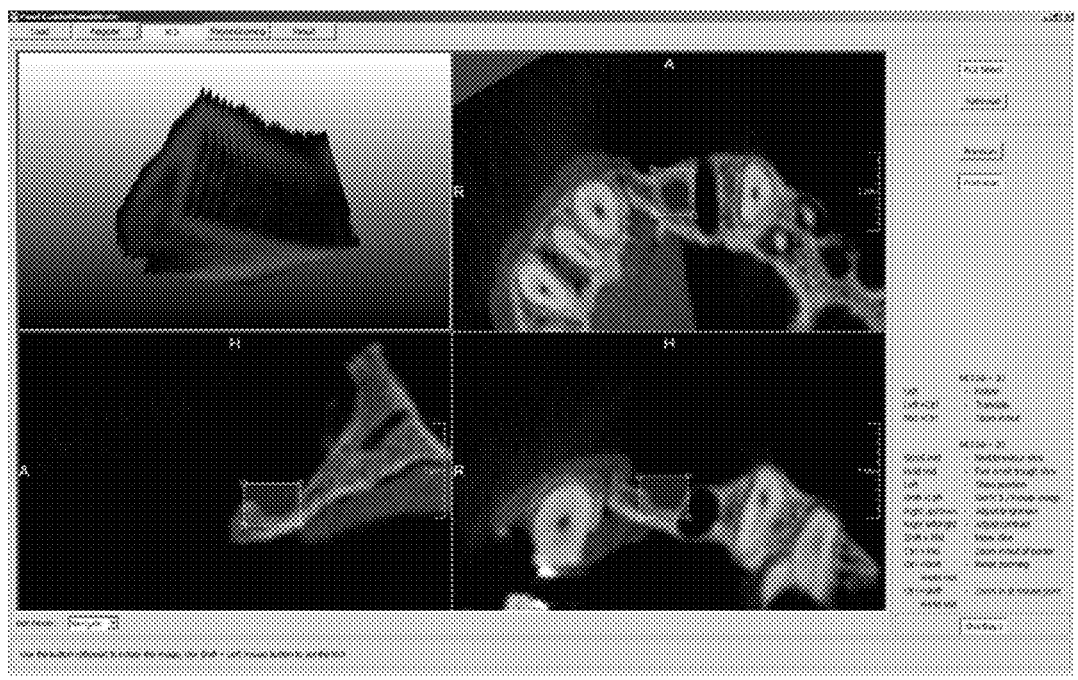
FIG. 13 illustrates selection the ROI using the clipping method wherein a rectangular box can adjusted on the three orthogonal views, as can be used in embodiments of the present invention.

The method advantageously comprises selecting the region of interest (ROI) automatically for both datasets, since they are both registered and "overlay" one another. However, before starting the selection of the ROI based on the clipping method described in more detail below, the scans can be "reformatted". This allows rotating the scans since the dental bony arches or jaws are curved and the clipping method using a selection box cannot be rotated along the jaws (see FIG. 12). The latter may be performed as advantageously one wants the clipping box to be parallel to the neighbouring teeth (see previously explained STRICS, where landmarks 3 in FIG. 6 are the neighbouring root surfaces, where the clipping planes 3 and 4 of FIG. 5 need to be placed). Next, the actual ROI can be selected using a rectangular box (see FIG. 13) on the three orthogonal slices (axial, sagittal and coronal). A 3D view of this clipping box is shown and helps to visualizes neighbouring clipping planes for easy landmarks selection.

In a fourth step, the exemplary method comprises segmentation of the bone. The segmentation may be performed by deleting a subset of data corresponding with air and/or soft tissue. The subset of data in a computed tomography image may correspond with a region, e.g. volumetric region, having a grey scale value lower than a predetermined value or corresponding with a majority of pixels having a grey scale value lower than a predetermined value. In this way, only the bony contour or volume of the region of interest is left. Different segmentation algorithms have been tested in-vitro and the most accurate results were obtained when using the region-growing algorithm. Seed points are placed in the air region of the selected ROI and neighbouring pixels (voxels) are automatically segmented. This can be attributed to the "outside". In this way, the grey zones (see FIG. 6) are segmented out. The seed points chosen in this grey zone will assign neighbouring pixels to the selected region by using a threshold value. The neighbouring pixels with the closest values to the chosen seed points (the closest grey value) will be assigned to the region and the threshold value determines the interval of grey values to be segmented. In the designed interface, the seed points are chosen on a 2D orthogonal slice (axial, sagittal or coronal). The threshold value for region growing can be selected in the right menu.

Figure 14:
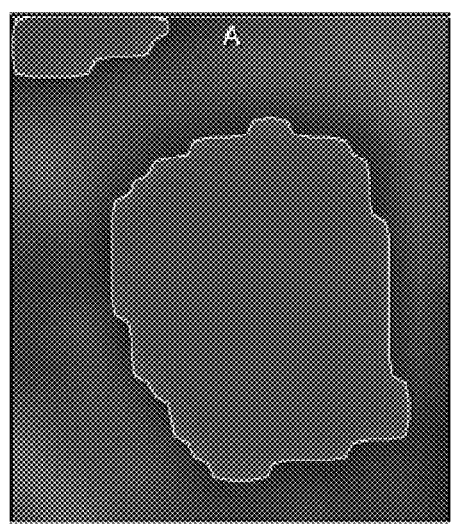
FIG. 14 illustrates the possibility for adjusting the region growing for small errors using more manual segmentation tools, as can be used in embodiments of the present invention.
Figure 14:
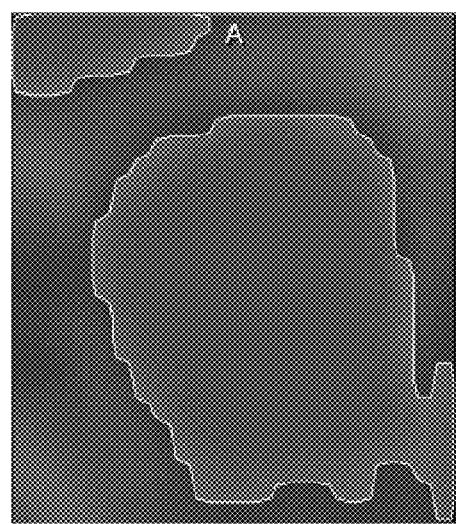
Figure 14:
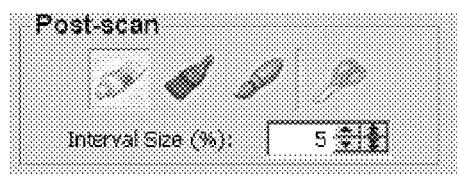
Figure 14:
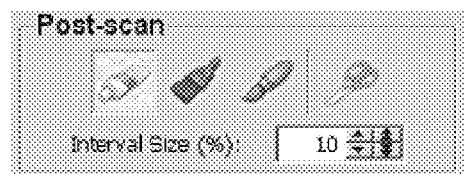

Following the region growing, the user can now check the segmented grey zones and if necessary, manually correct the segmentation for errors (see FIG. 14). Different additional tools may be provided for this, such as for example a paintbrush tool or bulge tool. A paintbrush tool is a circular brush tool (can be adjusted in size) that allows to manually correct for errors. Also a bulge tool is at hand which allows selecting the edges of the segmented region and move them to the desired edge. Corrections can be done on pre- and post-scan separately or in neighbouring windows, with the option to zoom in the region of interest.

Other segmentation tools also may be used (like simple or semi-automatic or adaptive thresholding) and help towards faster or improved (semi-) automatic segmentation with minimal user interaction.

In a fifth step, the volumes of the bone, or the bone with the soft tissue—depending on whether the soft tissue has been removed during segmentation—are calculated. The volumes then are subtracted from each other. The bone loss can be visualized in 3D and through a mm3 difference of both scans.

Figure 15:
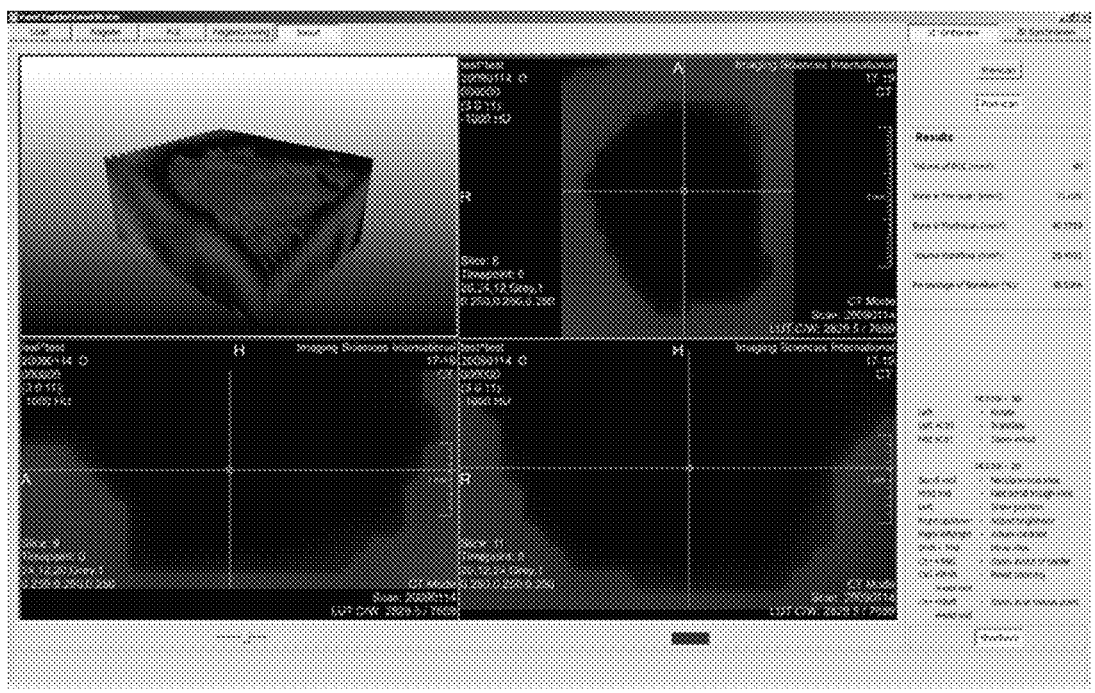
FIG. 15 illustrates a visualization module of a system for quantifying bone change, according to an embodiment of the present invention.

The method may be adapted for automatically calculating the total volume of the ROI, the volume of bone in pre- and post-scans, the volume of bone loss and the percentage of bone loss. In addition, these numerical values are complemented with a 3D visualization of the results (see FIG. 15).

The results can be shown in 2D orthogonal slices (axial, sagittal and coronal) which show by means of colours the segmented regions per scan (windows for pre- and post-scan separately). In addition, a 3D visualization of the overlaying bone with the region where bone loss has taken place, displayed in a colour.

In one aspect the present invention relates to a method for selecting a region of interest as such or a method for quantifying bone change including such a method for selecting a region of interest. The method may be referred to as Single Tooth Region of Interest Clipping Selection (STRICS), although embodiments of the present invention are not limited thereto.

The actual STRICS method uses the 3D ROI selection box in combination with anatomical landmarks of the neighbouring teeth (see FIG. 6, 7). In this way the ROI limits the volume to be segmented to the bone surrounding the tooth, implant or bone augmentation technique and the neighbouring information is left out to minimize segmentation mistakes caused by geometric distortion, artifacts or altered grey values of scan 1 and 2. A grey zone which represents air and soft tissues is present with the bone in the 3D ROI. This will be segmented out.

In some embodiments, the method comprises clipping using a particular clipping region. FIG. 5 is a schematic representation of the different clipping planes forming a 3D region of interest selection box. These clipping planes are two axial slices (inferior (1) and superior (2)), two sagittal slices (medial (3) and lateral (4)) and two coronal slices (anterior (5) and posterior (6)).

By way of illustration, below an example of a method for selecting a 3D region of interest according to embodiments of the present invention is discussed, embodiments not being limited thereto. The following exemplary description is for a bone volume ROI in the upper jaw (front, see FIG. 6), but can be used for all regions in both upper and lower jaw. In the present example, the method comprises clipping by defining six clipping planes, based on inherent landmarks. The following provides a description of how in the present example the clipping planes can be defined.

1) Cranial or Superior Clipping or Clipping of the Superior Data.

For this, the neighbouring roots should be evaluated and the superior axial slice should be set at the most caudal apex of the two neighbouring teeth (number 1 in FIG. 6). If in any case this apex is found to be too caudal, the most cranial apex can also be selected. If only one neighbour is present, the superior axial slice should (number 1 in FIG. 5) be set at this elements apex tip. Selection of these landmarks requires to scroll through the superior axial (with a superior-inferior view, number 1 in FIG. 5) and/or anterior coronal slices (number 5 in FIG. 5). Next the superior axial slice can be set at the right level.

If bone loss is expected to occur at a higher level (more cranial) than the roots, other anatomical landmarks than the neighbouring roots may be used.

Figure 8:
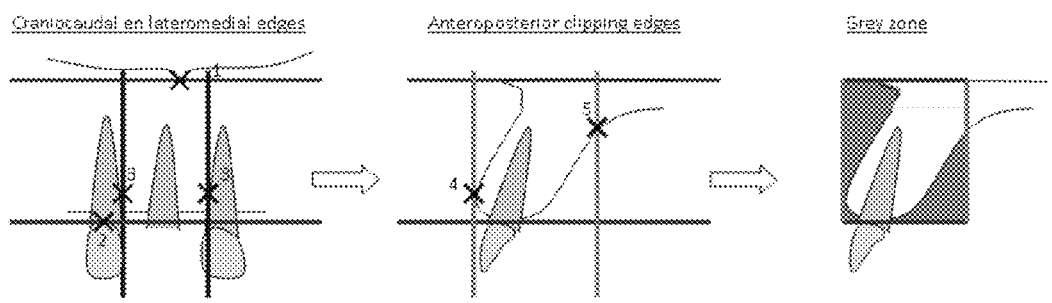
FIG. 8. illustrates a method for clipping a region of interest for the upper jaw (front-region) when bone loss or gain is expected more cranial of the root apices, as can be used in embodiments according to the present invention. 1=spina nasalis, 2=most cranial neighbouring tooth-cervix, 3=least medial and lateral contour of the neighbouring roots, 4=most buccal bone-edge, 5=most palatal bone-edge, grey zone=air and soft tissues covering the bone.
Figure 9:
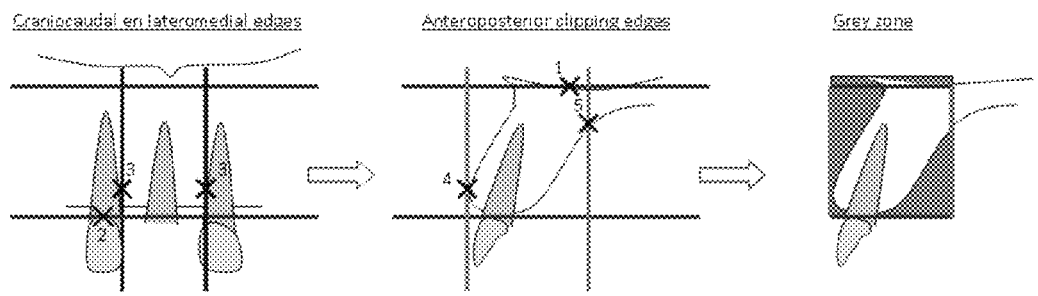
FIG. 9 illustrates a method for clipping a region of interest for the upper jaw (incisors) when bone loss or gain is expected more cranial of the root apices and when spina nasalis results in an added cranial non bony region of the ROI, as can be used in embodiments according to the present invention. 1=most caudal nasal cavity border, 2=most cranial neighbouring tooth-cervix, 3=least medial and lateral contour of the neighbouring roots, 4=most buccal bone-edge, 5=most palatal bone-edge, grey zone=air and soft tissues covering the bone.

For the incisor-canine (front) region, the spina nasalis can then be used (see FIG. 8) or the most caudal border of the nasal cavity in order to minimize inclusion of non-bony regions in the upper limit selected ROI (this can be checked on the sagittal slice, see FIG. 9). For the posterior premolar and molar regions, the same landmarks as the front region may used for cranial clipping or the inferior border of maxillary sinus.

2) Caudal or Inferior Clipping or Clipping of the Inferior Data.

For this, the neighbouring crowns should be evaluated. The inferior axial slice (number 2 in FIG. 5) should be set at the most cranial enamel border (tooth-cervix: border of enamel and cementum of the root or cemento-enamel junction (CEJ), number 2 in FIG. 6) of the neighbouring teeth. If in any case this cervix is found to be too cranial (and cutting of some alveolar bone), the most caudal cervix border can also be selected. Selection of these landmarks requires to scroll through the inferior axial slices (with an inferosuperior view, number 2 in FIG. 5) and/or anterior coronal slice (number 5 in FIG. 5). Next the axial slice (number 2 in FIG. 5) can be set at the right level.

3) Medial and Lateral Clipping, i.e. Clipping Medially and Laterally to the ROI

For this, the neighbouring root surfaces should be evaluated. The medial and lateral slices should both be set at the most approximating root surface to the volume of interest (number 3 in FIG. 6). If only one tooth is neighbouring, the second slice can be set at a neighbouring implant or the next tooth in line. Selection of these landmarks can be done by scrolling through the lateral and medial sagittal slices (numbers 3 and 4 in FIG. 5) and/or the anterior or posterior coronal slice (number 5 and 6 in FIG. 5).

4) Anterior Clipping or Clipping of the Anterior Coronal Slice.

For this, a sagittal view is taken, preferably the most lateral or medial view (number 3 or 4 in FIG. 5), and the anterior coronal slice (number 5 in FIG. 5) is set at the most buccal bony edge (number 4 in FIG. 6). For this selection, it may be required to scroll through the sagittal slice volume.

5) Posterior Clipping or Clipping of the Posterior Coronal Slice.

For this, the same view as in step 4) can be taken and the posterior coronal slice (number 6 in FIG. 5) is set at the most palatal (or lingual in case of the mandible) bony edge (number 5 in FIG. 6). For this selection too, it may be required to scroll through the sagittal slice volume.

If the nasopalatinal canal is in the selected ROI, it should be included and considered as bone. The cavity should preferably not be segmented out for inclusion in the grey zone. Another option is to exclude the bony region behind the nasopalatine canal: then the posterior clipping could occur at the most palatal or vestibular bony edge of the canal, or even diagonal perpendicular to the canal.

The posterior clipping will also depend on the selection of the cranial clipping plane (or caudal in case of the lower jaw): the most posterior bone which is part of the alveolar process can then be selected.

Figure 10:
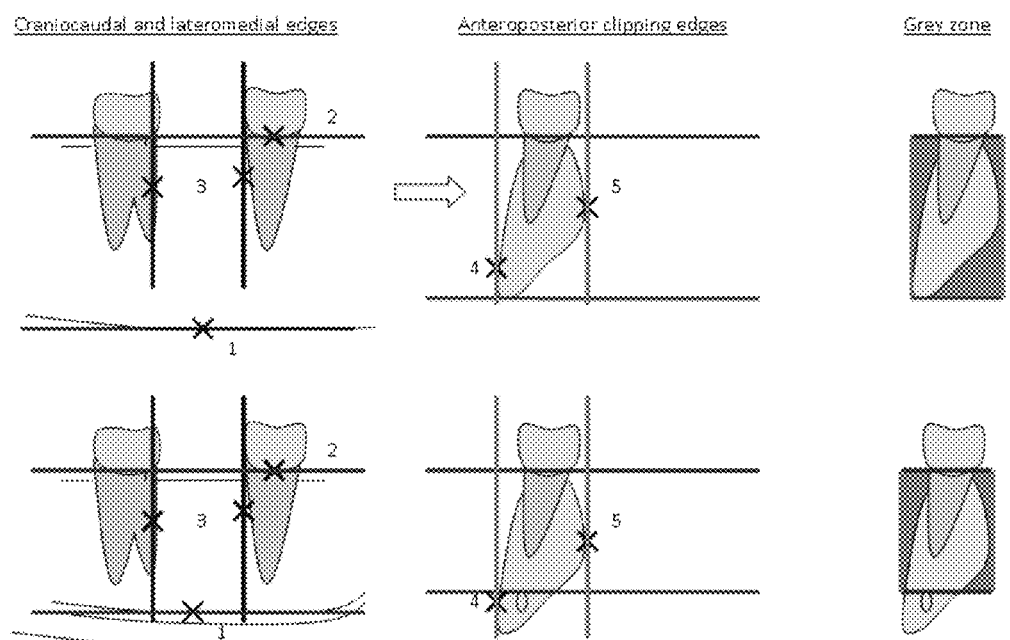
FIG. 10 illustrates a method for clipping a region of interest for the lower jaw (posterior) when bone loss or gain is expected more caudal of the root apices, as can be used in embodiments according to the present invention. 1=upper drawing: most cranial inferior border of the mandible; lower drawing: most cranial or superior border of the alveolar canal, 2=most caudal (inferior) neighbouring tooth-cervix, 3=approximating medial and lateral contour of the neighbouring roots, 4=most buccal bone-edge, 5=most lingual bone-edge, grey zone=air and soft tissues covering the bone.

The same applies for the lower jaw: the cranial clipping which is in the case of the lower jaw caudal clipping may be chosen using different anatomical landmarks if bone loss or gain is suspected more caudal than the neighbouring root apices. In this case, the inferior border of the mandible may be chosen or to minimize the grey zone, the superior or inferior border of the inferior alveolar canal or incisive canal (see FIG. 10). In the front region, the genial tubercles can also be used. But also the superior or inferior borders of the mental foramen are possible.

The method may also be applied to follow up bone around multiple teeth just by changing lateral and medial clipping planes and moving to the next neighbouring teeth. The STRICS method may then rather be called MULTI-TRICS method to indicate multiple teeth.

Figure 11:
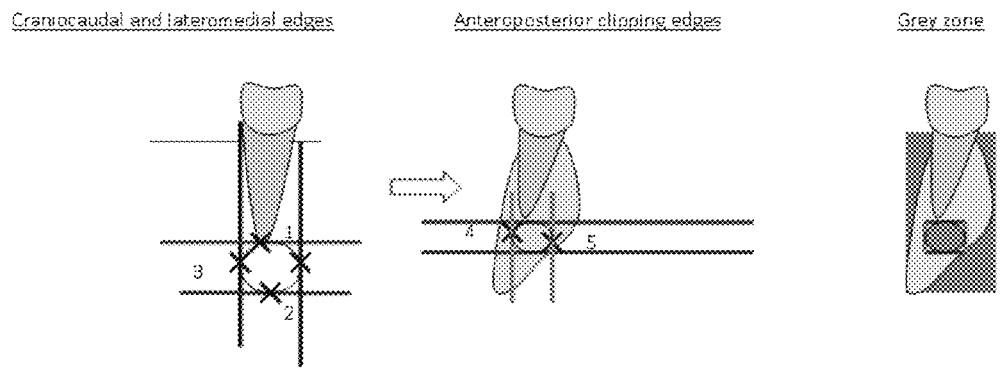
FIG. 11 illustrates a method for clipping a region of interest for radiolucent lesions, as can be used in embodiments according to the present invention. 1 and 2=most cranial (superior) and caudal (inferior) edge of the radiolucent lesion, 3 and 4=most buccal and oral edge of the radiolucent lesion, grey zone=air and soft tissues inside the radiolucent region.

Furthermore, the STRICS method may also be applied to follow-up bony changes around radiolucent lesions (with or without relation to a tooth). The latero-medial, cranio-caudal and antero-posterior clipping then solely depends on selecting the most lateral, medial, cranial, caudal, anterior and posterior border of the lesion (see FIG. 11). Only here, the grey zone will be the radiolucency itself, which can be segmented out. Bony changes around the lesions, and indirectly the lesions themselves can thus be followed-up. The selection of the lesion borders and clipping may also be done after rotating the volume to align sagittal and coronal slices parallel to the axis of the tooth and the axial plane perpendicular to this tooth. This may avoid excluding desired bony regions or including unwanted structures in the ROI. The oral and buccally oriented levels of the radiolucent region can be extended to their respective alveolar cortical borders and similary, the cranio-caudal edges may be extended to the inferior border of the mandible and neighbouring tooth apices or for the upper jaw the inferior maxillary sinus border or nasal cavity and the neighbouring tooth apices.

Similarly, for other applications like cleft palate and lip, other landmarks may be chosen to determine an adequate ROI. For instance, when no teeth are present (edentulous region or patient), it may be desirable to follow-up bone around a bone graft, which will also require slightly modified landmarks. The STRICS method should than rather be called BRICS referring to "Bone Region of Interest Clipping Selection". For this, it will be possible to use the same anatomical landmarks as mentioned before, but for the superior (lower jaw) or inferior (upper jaw) clipping plane we may choose the most cranial (lower jaw) or caudal (upper jaw) alveolar crest point and for the mesial and distal clipping axes we may choose freely within the arch (per zone: molar-premoral-canine-incisors) or at specified distances from the desired region. Because of the interactive scrolling through slices for adequate ROI selection, it is important to be able to view the ROI as a 3D cube (see FIG. 5), which allows to see the clipping plane slices. In this way, when the ROI is selected through the bounding box on the 2D slices, the cube is visible in 3D with the neighbouring boundaries visible for landmark selection. ROI selection without this would be more difficult. However, other configurations of this ROI may be used, even using a diagonal clipping plane, as an alternative to rotating the original volume (pre-scan).

Figure 7:
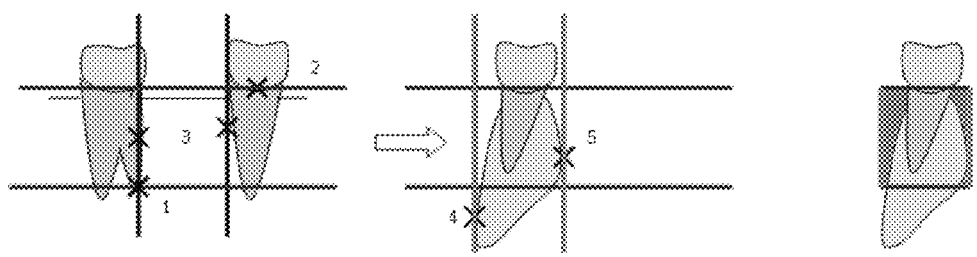
FIG. 7 illustrates a method for clipping a region of interest for the lower jaw (posterior) as can be used in embodiments according to the present invention. 1=most cranial (superior) neighbouring tooth-apex, 2=most caudal (inferior) neighbouring tooth-cervix, 3=approximating medial and lateral contour of the neighbouring roots, 4=most buccal bone-edge, 5=most lingual bone-edge, grey zone=air and soft tissues covering the bone.

The STRICS method can also be applied to any region in the jaw, both upper and lower jaws. For instance, FIG. 7 is a schematic representation of the STRICS method in the lower jaw, posterior area. The anatomical landmarks are chosen in the same way (except that cranial and caudal become caudal and cranial respectively). Also, if it is desired to include the soft tissue changes surrounding the desired bony region, it suffices to segment out the air and not the soft tissues. The most buccal and oral clipping planes, and the most caudal or cranial ones are then determined by the extremities of the soft tissues.

The clipping (which is actually only a visualization tool) should then be followed by cropping of the data, a process where the information that was made invisible in the clipping, is deleted. In the designed user-interface below, only the automatically cropped data is used for the following steps.

In one aspect, the present invention relates to a system for volumetric quantification of local bone changes. The system may be especially suitable for performing a method for volumetric quantifying as described above, although embodiments are not limited thereto. The system comprises an input means for receiving at least a first and second computed tomography data sets representative of a three dimensional image. The computed tomography data sets may be three dimensional images or scans. The system also comprises a processing means configured for registering the at least first and second computed tomography three dimensional image. The processor further is configured for selecting a region of interest in one of the first or the second computed tomography three dimensional image and for segmenting the local bone within the region of interest in the first computed tomography three dimensional image and the second computed tomography three dimensional image, by segmenting the grey zones related to air and/or soft tissues within the region of interest and attributing the greyzones to an outside region, while defining the remaining volume as representing the local bone or the local bone with soft tissue. The processor furthermore is adapted for calculating the volume of the local bone or the local bone with soft tissue in the first and the second tomographic three dimensional image and subtracting the first volume from the second volume thereby defining the difference as the local bone change or the change in local bone with soft tissue. The system furthermore comprises an output means for outputting the local bone change or the change in local bone with soft tissue. Such an output may for example be a graphical output and/or a numerical output. The system may furthermore comprise features for performing steps or part thereof of the method for volumetric quantification of bone loss as described above. The system may be implemented as hardware or as software. It may be implemented in a computing system. The system may comprise an easy-to-use user interface that is configured for initiating or providing instructions for performing the several steps for accurate bone follow-up. One example of such an interface may be an interface programmed in the MevisLab® programming environment, wherein instructions can be provided or results can be shown for the different steps under different "Tabs". The different outputs under the tabs may be similar to or as shown by way of example for the exemplary method described above.

In a further aspect, the present invention relates to a computer program product for, when executing on a processing means, for example in a device according to the above described aspect of the invention, carrying out one of the methods for quantifying bone change or for determining a region of interest as described above. In other words, methods according to embodiments of the present invention may be implemented as computer-implemented methods, e.g. implemented in a software based manner. One example of a processing system may be a processing system that includes at least one programmable processor coupled to a memory subsystem that includes at least one form of memory, e.g., RAM, ROM, and so forth. It is to be noted that the processor or processors may be a general purpose, or a special purpose processor, and may be for inclusion in a device, e.g., a chip that has other components that perform other functions. Thus, one or more aspects of embodiments of the present invention can be implemented in digital electronic circuitry, or in computer hardware, firmware, software, or in combinations of them. The processing system may include a storage subsystem that has at least one disk drive and/or CD-ROM drive and/or DVD drive. In some implementations, a display system, a keyboard, and a pointing device may be included as part of a user interface subsystem to provide for a user to manually input information. Ports for inputting and outputting data also may be included. More elements such as network connections, interfaces to various devices, and so forth, may be included. The various elements of the processing system may be coupled in various ways, including via a bus subsystem, in the present example for simplicity a single bus, but will be understood to those skilled in the art to include a system of at least one bus. The memory of the memory subsystem may at some time hold part or all of a set of instructions that when executed on the processing system implement the steps of the method embodiments described herein.

In further aspects, the present invention relates to a data carrier for storing a computer program product as described above or to the transmission of a computer program product over a wide or local area network. Such a data carrier can thus tangibly embody a computer program product as described above. The carrier medium therefore may carry machine-readable code for execution by a programmable processor. The present invention thus relates to a carrier medium carrying a computer program product that, when executed on computing means, provides instructions for executing any of the methods for quantifying bone change or determining a region of interest as described above. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Common forms of computer readable media include, a CD-ROM, a DVD, a flexible disk or floppy disk, a tape, a memory chip or cartridge or any other medium from which a computer can read. Various forms of computer readable media may be involved in carrying one or more sequences of one or more instructions to a processor for execution. The computer program product can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fibre optics, including the wires that comprise a bus within a computer.

In still another aspect, the present invention relates to an image or volumetric image obtained by a method for quantifying bone change or identifying a region of interest as described above.

EXAMPLE 1

Figure 16:
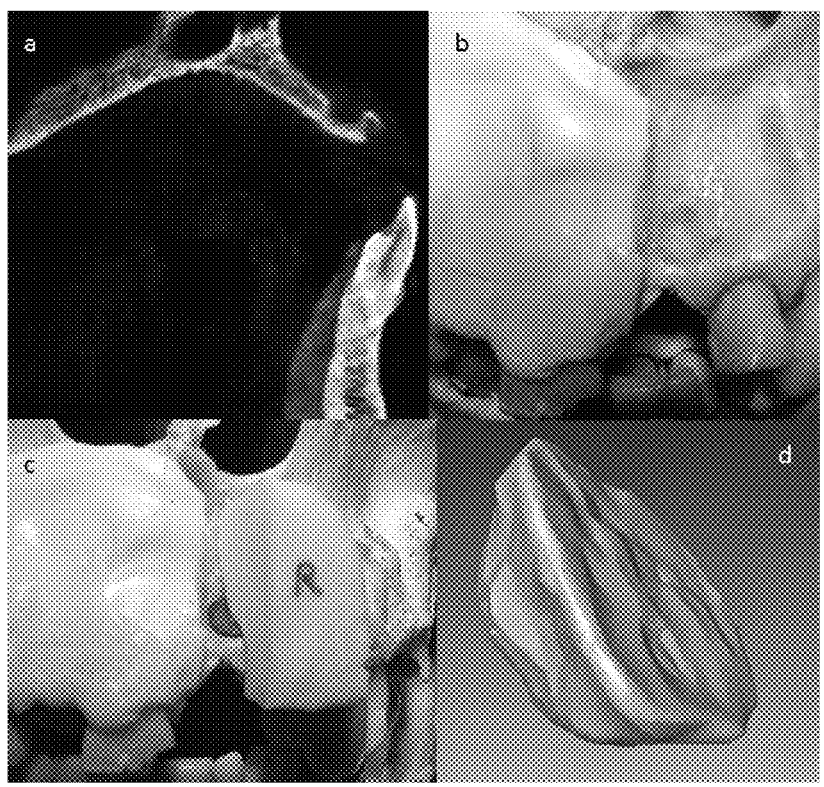
FIG. 16 illustrates an example of an in-vitro experiment illustrating features of embodiments according to the present invention. A) Sagittal CBCT scan with the created defect in the upper jaw. B) Clinical frontal view of the convergent defect. C) The defect filled with green stent material using a buccal Optosil key. D) Triangulated surface model of the optically scanned bone defect negative (green stent).

By way of illustration, embodiments of the present invention not being limited thereby, an experimental example is discussed below, illustrating features and advantages of embodiments of the present invention. The example illustrates, for the determination of the bone volume follow-up method, an in-vitro pre-test whereby accuracy is evaluated (see FIG. 16). A dry skull with soft tissue simulation modelled over the jaws served as subject. A defect was created with a round steal bur at the maxillary left central incisor level to simulate bone loss. A pre-scan was first taken before defect creation. After defect creation (with buccal occlusal keys to preserve the buccal contour), heated wax modelled into the defect and covered with the buccal key. In this wax, a negative of the defect could be created. Then, the obtained defect key was optically scanned with a laser scanner at a resolution of approximately 40 micron. Now the volume of the defect could be calculated in mm3 and a post CBCT scan taken for bone volume follow-up.

Both PRE and POST CBCT scans were imported into Amira® (in DICOM format), a commercially available image analysis software.

Figure 17:
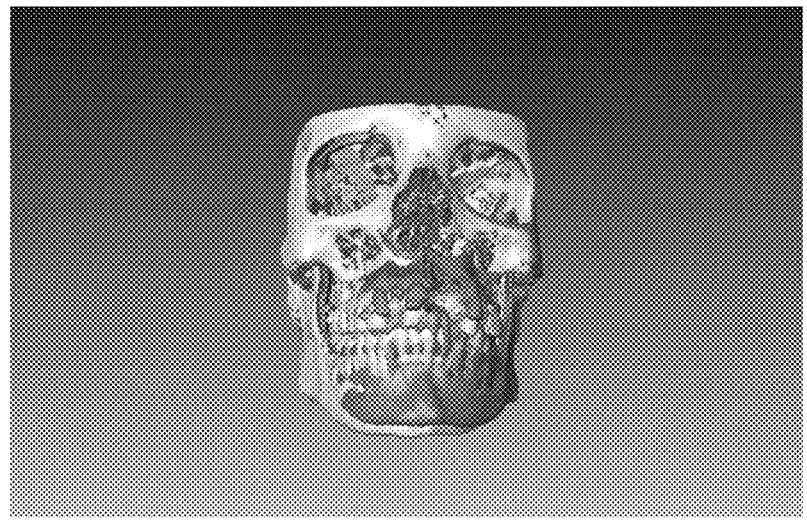
FIG. 17 illustrates the step of pre- and post-scan loading into Amira®, according to an example of a method for bone change quantification according to an embodiment of the present invention. The two bone volumes can be displayed, which reveals misalignment of scan 2 compared to scan 1.
Figure 18:
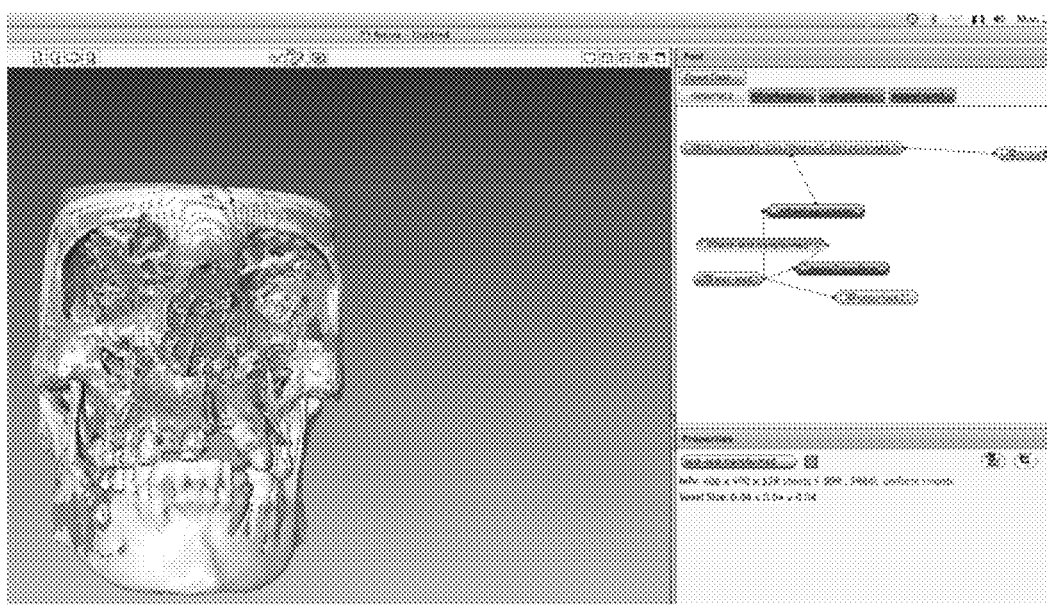
FIG. 18 illustrates the step of registering of two scans in Amira®, according to an example of a method for bone change quantification according to an embodiment of the present invention.

After the scans were loaded, an option was chosen "isosurface" to create two surface models of the pre and post scans. This reveals misalignment of the two scans (see FIG. 17). When working without registration of the two volumes, ROI selection of both bone volumes in scan 1 and 2, was very user-dependent, prone to errors and time consuming. Therefore, the scans were registered. After registration of scan 2 with 1, scan two was transformed to validate (or lock) the registration (see FIG. 18, the network in the right panel is quite complicated, especially for inexperienced users).

Figure 19:
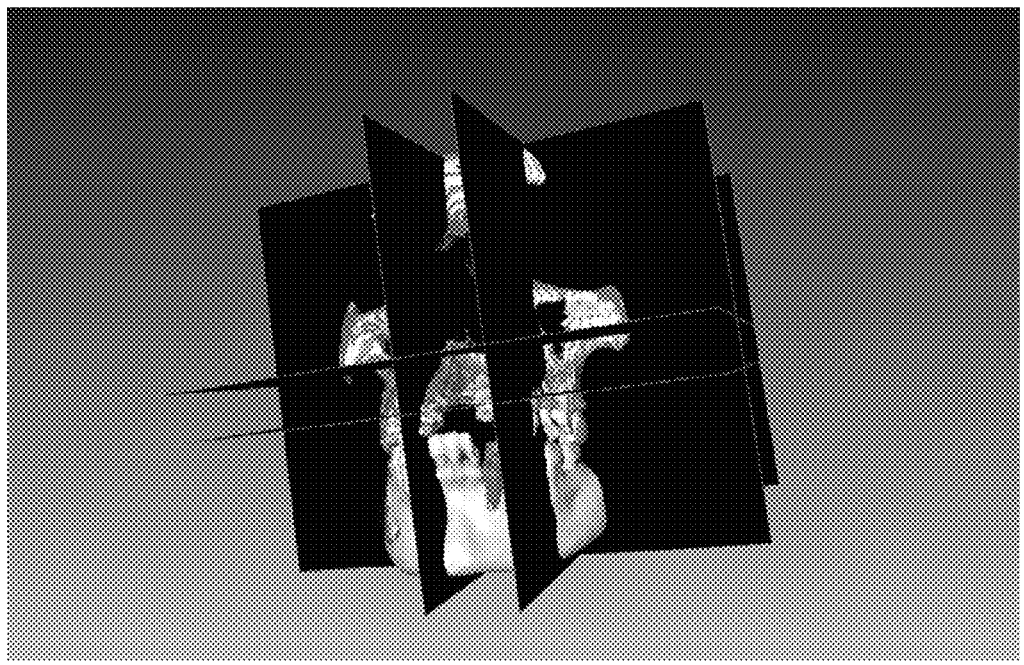
FIG. 19 illustrates the step of determining clipping planes, according to an example of a method for bone change quantification according to an embodiment of the present invention.

The next step was selecting 6 orthogonal slices to select or region of interest and clip the data. In this platform, the selection of all slices, and the application of the STRICS method is very time-consuming (see FIG. 19).

Figure 20:
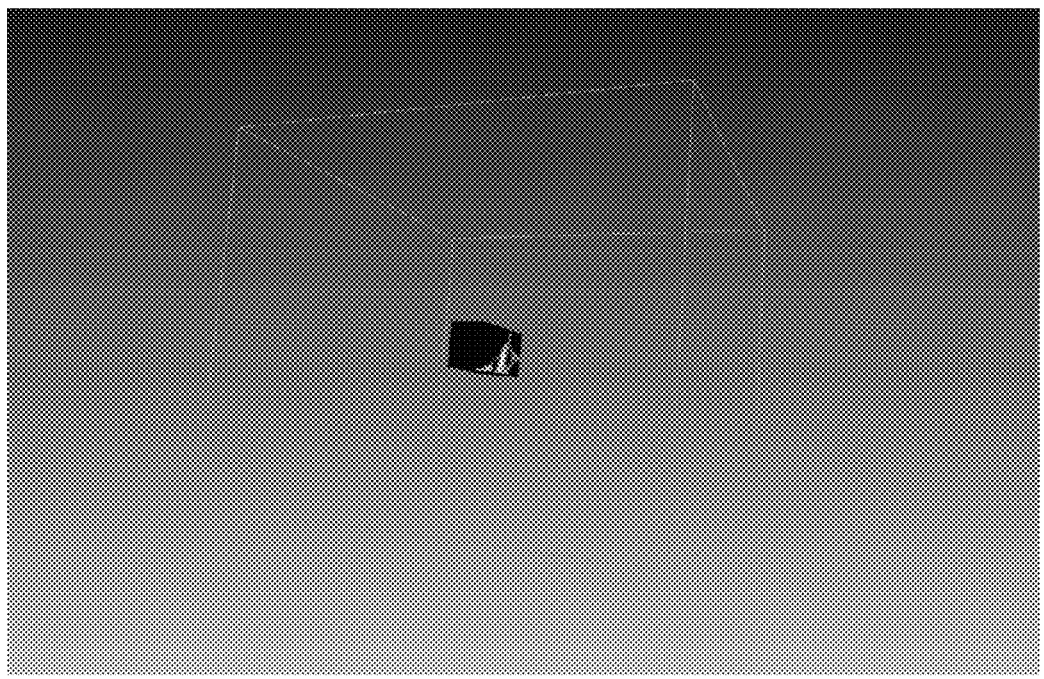
FIG. 20 illustrates the step of cropping of the 3D cube whereby the ROI is selected based on landmarks, according to an example of a method for bone change quantification according to an embodiment of the present invention.

After clipping the data to obtain a 3D cube (see FIG. 20), the bounding boxes of the two volumes needed to be adjusted to the clipped volumes, in order to transform the data volumes and cut off the unwanted information (=cropping). All these steps were automated in the designed user interface mentioned.

The last steps were segmentation of the bone volumes on both scans and the calculation of the volumes. In this research, simple thresholding, manual slice by slice segmentation and region growing have been tested. The latter, followed by small manual corrections on the 2D slices of the cropped ROI, was the closest to the gold standard (only approximately 5 mm3 deviation).

The invention claimed is:

1. A method for volumetric quantification of local bone changes comprising the steps of:
loading at least a first and second computed tomography three dimensional image,
registering said at least first three dimensional image and second three dimensional image to one coordinate system,
selecting a region of interest in one of said first three dimensional image or said second three dimensional image,
for said first three dimensional image and said second three dimensional image, segmenting the local bone within the region of interest by segmenting voxels related to air and/or soft tissues within the region of interest and attributing these voxels to an outside region, while the volume formed by the remaining volume represent the local bone or the local bone with soft tissue, and
calculating the volume of local bone in the first three dimensional image and the volume of local bone in said second three dimensional image and subtracting said first volume from said second volume and defining the difference as the local bone change or the change in local bone with soft tissue,
wherein said selecting of the region of interest comprises the steps:
selecting a set of anatomical landmarks in one of said first three dimensional image or second three dimensional image,
determining a set of clipping planes which construct a volume forming the region of interest in the respective three dimensional image on the basis of said anatomical landmarks, and
removing all data from the respective three dimensional image outside the region of interest.

2. The method according to claim 1, wherein determining a set of clipping planes comprises determining a set of 6 clipping planes.

3. The method according to claim 1 wherein selecting the anatomical landmarks comprises selecting at least one or a combination of:
a first landmark that is a most caudal or cranial root apex of teeth neighbouring the local bone volume to be determined,
a second landmark that is a most cranial or caudal tooth cervix of a teeth neighbouring the local bone volume to be determined, so that, if an alveolar crest is missing partly in the region of interest, a most caudal or cranial tooth cervix can be chosen,
a third and fourth landmarks being most proximal edges of a teeth's roots neighbouring the local bone volume to be determined, so that in case of a neighbouring implant body existing, a most proximal edge of the implant body or its abutment can be chosen in such a way that no metal of the implant body is present in the final region of interest and so that in case a direct neighbour is missing, a next element in the arch can be used for the landmarks selection,
a fifth landmark being a most buccal bony edge of the region of interest,
a sixth landmark being a most oral bony edge of the region of interest.

4. The method according to claim 3 wherein selecting the anatomical landmarks comprises selecting at least all of:
a first landmark that is a most caudal or cranial root apex of the teeth neighbouring the local bone volume to be determined,
a second landmark that is a most cranial or caudal tooth cervix of a teeth neighbouring the local bone volume to be determined, so that, if an alveolar crest is missing partly in the region of interest, a most caudal or cranial tooth cervix can be chosen,
a third and fourth landmarks being most proximal edges of a teeth's roots neighbouring a local bone volume to be determined, so that in case of a neighbouring implant body, a most proximal edge of the implant body or its abutment can be chosen in such a way that no metal of the implant body is present in the final region of interest and so that in case a direct neighbour is missing, a next element in the arch can be used for a landmarks selection, a fifth landmark being a most buccal bony edge of the region of interest, a sixth landmark being a most oral bony edge of the region of interest.

5. The method according to claim 4 wherein the landmarks for an upper jaw comprise the spina nasalis or inferior border of the nasal cavity or maxillary sinus, and/or the landmarks for a lower jaw comprise an inferior mandibular cortical border, inferior or superior border of an inferior alveolar canal, incisive canal or mental foramen or genial tubercles.

6. The method according to claim 1 wherein selecting a set of anatomical landmarks comprises taking into account whether bone change is followed for a case where no teeth are present.

7. The method according to claim 1 wherein selecting a set of anatomical landmarks comprises taking into account whether bone change is followed around radiolucent lesions of jaws, including periapical lesions.

8. The method according to claim 1, wherein selecting a set of anatomical landmarks comprises taking into account whether bone change is followed such that soft tissues surrounding the local bone is included in the region of interest.

9. A method according to claim 3, including determining clipping planes by determining at least one or a combination of:

a first clipping plane being constructed by defining a plane through a first landmark point said plane parallel with the axial direction, a second clipping plane being constructed by defining a plane through a second landmark point said plane parallel with the axial direction, a third and fourth clipping plane being constructed by defining a plane through a third landmark point parallel with the sagittal direction and a plane through the fourth landmark points parallel with the sagittal direction, a fifth clipping plane being constructed by defining a plane through a fifth landmark point said plane parallel with the coronal direction, a sixth clipping plane being constructed by defining a plane through a sixth landmark point said plane parallel with the coronal direction.

10. A method according to claim 3, wherein selecting the set of landmarks comprises selecting said six landmarks and wherein determining clipping planes comprises determining all of:

a first clipping plane being constructed by defining a plane through the first landmark point said plane parallel with the axial direction, second clipping plane being constructed by defining a plane through the second landmark point said plane parallel with the axial direction, a third and fourth clipping plane being constructed by defining a plane through the third landmark point parallel with the sagittal direction and a plane through the fourth landmark points parallel with the sagittal direction, a fifth clipping plane being constructed by defining a plane through the fifth landmark point said plane parallel with the coronal direction, a sixth clipping plane being constructed by defining a plane through the sixth landmark point said plane parallel with the coronal direction.

11. A system for volumetric quantification of local bone changes, the system comprising an input means arranged to receive at least a first and second computed tomography three dimensional image, a processing means configured to register the at least first and second computed tomography three dimensional image, select a region of interest in one of the first or the second computed tomography three dimensional image, in which said selecting of the region of interest comprises selecting a set of anatomical landmarks in said one of the first or the second computed tomography three dimensional image, determining a set of clipping planes which construct a volume forming the region of interest in said one of the first or the second computed tomography three dimensional image on the basis of said anatomical landmarks, and removing all data from said one of the first or the second computed tomography three dimensional image outside the region of interest, segmenting local bone within the region of interest in the first computed tomography three dimensional image and the second computed tomography three dimensional image, by segmenting voxels related to at least one of air and soft tissues within the region of interest and attributing the voxels to an outside region, while defining the remaining volume as representing local bone or local bone with soft tissue, and calculating the volume of local bone or local bone with soft tissue in the first and the second tomographic three dimensional image and substracting the first volume from the second volume thereby defining the difference as a local bone change or a change in local bone with soft tissue, and an output means arranged to output the local bone change or the change in local bone with soft tissue.

12. The system according to claim 11, the system being configured to perform a method according to claim 1.

13. A method for selecting a region of interest in a computed tomography three dimensional image comprising the steps:

selecting a set of anatomical landmarks in the computed tomography three dimensional image, determining a set of clipping planes which construct a volume forming the region of interest in the three dimensional image on the basis of said anatomical landmarks, and removing all data from the three dimensional image outside the region of interest, wherein selecting the anatomical landmarks comprises selecting at least one or a combination of: a first landmark that is a most caudal or cranial root apex of teeth neighbouring a local bone volume to be determined, a second landmark that is a most cranial or caudal tooth cervix of a teeth neighbouring the local bone volume to be determined, so that, if an alveolar crest is missing partly in the region of interest, a most caudal or cranial tooth cervix can be chosen, a third and fourth landmarks being most proximal edges of a teeth's roots neighbouring the local bone volume to be determined, so that in case of a neighbouring implant body, a most proximal edge of the implant body or its abutment can be chosen in such a way that no metal of the implant is present in the final region of interest and so that in case a direct neighbour is missing, a next element in the arch can be used for the landmarks selection. a fifth landmark being a most buccal bony edge of the region of interest, and a sixth landmark being a most oral bony edge of the region of interest.

14. The method according to claim 13, wherein determining clipping planes comprises determining at least one or more of:
 a first clipping plane being constructed by defining a plane through a first landmark point said plane parallel with the axial direction,
 second clipping plane being constructed by defining a plane through a second landmark point said plane parallel with the axial direction,
 a third and fourth clipping plane being constructed by defining a plane through a third landmark point parallel with the sagittal direction and a plane through the fourth landmark points parallel with the sagittal direction,
 a fifth clipping plane being constructed by defining a plane through a fifth landmark point said plane parallel with the coronal direction,
 a sixth clipping plane being constructed by defining a plane through a sixth landmark point said plane parallel with the coronal direction.

15. A non-transitory computer program product that, when executed on a processor, carries out a method for selecting a region of interest in a computed tomography three dimensional image that comprises the steps of:
 selecting a set of anatomical landmarks in the computed tomography three dimensional image,
 determining a set of clipping planes which construct a volume forming the region of interest in the three dimensional image on the basis of said anatomical landmarks, and
 removing all data from the three dimensional image outside the region of interest,
 the computer program product containing instructions for carrying out the steps of:
 loading at least a first and second computed tomography three dimensional image, registering said at least a first three dimensional image and second three dimensional image to one coordinate system,
 applying said steps in order to select a region of interest in one of said first three dimensional image or said second three dimensional image,
 for said first three dimensional image and said second three dimensional image, segmenting local bone within the region of interest by segmenting voxels related to either or both air and soft tissues within the region of interest and attributing these voxels to an outside region, while the volume formed by a remaining volume represent the local bone or the local bone with soft tissue, and calculating the volume of local bone in the first three dimensional image and the volume of local bone in said second three dimensional image and subtracting said first volume from said second volume and defining the difference as the local bone change or the change in local bone with soft tissue.

* * * * *